(12) United States Patent
Meyer et al.

(10) Patent No.: US 11,954,578 B2
(45) Date of Patent: Apr. 9, 2024

(54) DENOISING MAGNETIC RESONANCE IMAGES USING UNSUPERVISED DEEP CONVOLUTIONAL NEURAL NETWORKS

(71) Applicant: UNIVERSITY OF VIRGINIA PATENT FOUNDATION, Charlottesville, VA (US)

(72) Inventors: Craig H Meyer, Charlottesville, VA (US); Xue Feng, Charlottesville, VA (US)

(73) Assignee: UNIVERSITY OF VIRGINIA PATENT FOUNDATION, Charlottesville, VA (US)

( * ) Notice: Subject to any disclaimer, the term of this patent is extended or adjusted under 35 U.S.C. 154(b) by 347 days.

(21) Appl. No.: 17/605,078

(22) PCT Filed: Apr. 24, 2020

(86) PCT No.: PCT/US2020/029866
§ 371 (c)(1),
(2) Date: Oct. 20, 2021

(87) PCT Pub. No.: WO2020/219915
PCT Pub. Date: Oct. 29, 2020

(65) Prior Publication Data
US 2022/0188602 A1 Jun. 16, 2022

Related U.S. Application Data

(60) Provisional application No. 62/837,874, filed on Apr. 24, 2019.

(51) Int. Cl.
*G06N 3/045* (2023.01)
*A61B 5/055* (2006.01)
(Continued)

(52) U.S. Cl.
CPC ............ *G06N 3/045* (2023.01); *A61B 5/055* (2013.01); *G01R 33/5608* (2013.01);
(Continued)

(58) Field of Classification Search
CPC ........ G06N 3/045; G06N 3/047; G06N 3/088; A61B 5/055; A61B 5/7203;
(Continued)

(56) References Cited

U.S. PATENT DOCUMENTS 9,569,843 B1 * 2/2017 Mailhe ...................... G06T 5/20
10,140,544 B1 * 11/2018 Zhao ...................... G06N 20/00
(Continued)

FOREIGN PATENT DOCUMENTS

CN 107507149 A * 12/2017
JP 2020101910 A * 7/2020 ........... G06N 3/0454
(Continued)

OTHER PUBLICATIONS

Aja-Fernandez S, Vegas-Sanchez-Ferrero G, Tristan-Vega A. Noise estimation in parallel MRI: GRAPPA and SENSE. Magn Reson Imaging. 2014;32(3):281-290. doi: 10.1016/j.mri.2013.12.001.
(Continued)

*Primary Examiner* — Mahendra R Patel
(74) *Attorney, Agent, or Firm* — Meunier Carlin & Curfman LLC

(57) ABSTRACT

Systems and methods for denoising a magnetic resonance (MR) image utilize an unsupervised deep convolutional neural network (U-DCNN). Magnetic resonance (MR) image data of an area of interest of a subject can be acquired, which can include noisy input images that comprise noise data and noise free image data. For each of the noisy input images, iterations can be run of a converging sequence in an unsupervised deep convolutional neural network. In each iteration, parameter settings are updated; the parameter
(Continued)

settings are used in calculating a series of image feature sets with the U-DCNN. The image feature sets predict an output image. The converging sequence of the U-DCNN is terminated before the feature sets predict a respective output image that replicates all of the noise data from the noisy input image. Based on a selected feature set, a denoised MR image of the area of interest of the subject can be output.

22 Claims, 8 Drawing Sheets

(51) Int. Cl.
*G01R 33/56* (2006.01)
*G06N 3/047* (2023.01)
*G06N 3/088* (2023.01)
*G06T 5/00* (2006.01)

(52) U.S. Cl.
CPC .............. *G06N 3/047* (2023.01); *G06N 3/088* (2013.01); *G06T 5/002* (2013.01); *G06T 2200/04* (2013.01); *G06T 2207/10092* (2013.01); *G06T 2207/30016* (2013.01)

(58) Field of Classification Search
CPC . G01R 33/5608; G06T 5/002; G06T 2200/04; G06T 2207/10092; G06T 2207/30016; G06T 2207/10088
USPC ......................................................... 382/157
See application file for complete search history.

(56) References Cited

U.S. PATENT DOCUMENTS

| | | | | |
|---|---|---|---|---|
| 10,698,063 | B2 * | 6/2020 | Braun | G06N 3/08 |
| 10,915,990 | B2 * | 2/2021 | Lebel | G06T 5/002 |
| 11,574,170 | B2 * | 2/2023 | Isogawa | G06N 3/048 |
| 2010/0002929 | A1 * | 1/2010 | Sammak | G06T 7/0014 382/133 |
| 2013/0322728 | A1 * | 12/2013 | Jacobs | G06T 7/0012 382/132 |
| 2017/0213321 | A1 * | 7/2017 | Matviychuk | G06V 10/7715 |
| 2017/0323481 | A1 * | 11/2017 | Tran | H04N 23/611 |
| 2018/0349759 | A1 * | 12/2018 | Isogawa | G06N 3/045 |
| 2018/0374245 | A1 * | 12/2018 | Xu | A61B 6/4085 |
| 2019/0019317 | A1 * | 1/2019 | Zhang | A61B 6/5205 |
| 2019/0030371 | A1 * | 1/2019 | Han | A61N 5/1039 |
| 2019/0057521 | A1 * | 2/2019 | Teixeira | A61B 90/361 |
| 2019/0108441 | A1 * | 4/2019 | Thibault | G06T 11/003 |
| 2020/0065940 | A1 * | 2/2020 | Tang | G06T 3/40 |
| 2020/0234080 | A1 * | 7/2020 | Ciller Ruiz | G06N 3/08 |
| 2020/0311878 | A1 * | 10/2020 | Matsuura | G06V 10/82 |

FOREIGN PATENT DOCUMENTS

| | | | | |
|---|---|---|---|---|
| JP | 7138113 | B2 * | 9/2022 | ............ A61B 5/7203 |
| WO | WO-2014093320 | A1 * | 6/2014 | ............ A61B 5/055 |
| WO | WO-2015017632 | A1 * | 2/2015 | ............ A61B 5/055 |
| WO | 2017223560 | A1 | 12/2017 | |
| WO | WO-2017223560 | A1 * | 12/2017 | ............... A61B 5/00 |
| WO | 2018106805 | A1 | 6/2018 | |
| WO | WO-2018106805 | A1 * | 6/2018 | .......... G06K 9/6274 |
| WO | WO-2018210978 | A1 * | 11/2018 | .......... G06K 9/6256 |
| WO | 2019005722 | A1 | 1/2019 | |
| WO | WO-2019005722 | A1 * | 1/2019 | ............ G06K 9/4628 |
| WO | WO-2019183584 | A1 * | 9/2019 | ............ A61B 6/032 |

OTHER PUBLICATIONS

Benou A, Veksler R, Friedman A, Riklin Raviv T. Ensemble of expert deep neural networks for spatio-temporal denoising of contrast-enhanced MRI sequences. Med Image Anal. 2017;42:145-159. doi:10.1016/j.media.2017.07.006.

Bhujle HV, Chaudhuri S. Laplacian based non-local means denoising of MR images with rician noise. Magn Reson Imaging. 2013;31(9):1599-1610. doi: 10.1016/j.mri.2013.07.001.

BrainWeb: Simulated Brain Database http://www.bic.mni.mcgill.ca/brainweb/.

Buades A, Coll B, Morel J. A non-local algorithm for image denoising. In Proc. 2005 IEEE Computer Society Conference on Computer Vision and Pattern Recognition (CVPR'05), San Diego, CA, USA, 2005, pp. 60-65, vol. 2. doi: 10.1109/CVPR.2005.38.

Buades, A., Coll, B., Morel, J.-M.: Non-Local Means Denoising. Image Processing On Line. 1, (2011).

Chang L, ChaoBang G, Xi Y. A MRI denoising method based on 3D nonlocal means and multidimensional PCA. Comput Math Methods Med. 2015;232389. doi: 10.1155/2015/232389.

Çiçek, Özgün et al., 3D U-Net: Learning Dense Volumetric Segmentation from Sparse Annotation published in MICCAI 2016.

Cocosco CA, Kollokian V, Kwan RK, Evans AC. BrainWeb: Online Interface to a 3D MRI Simulated Brain Database. NeuroImage, 1997;5(4):S425.

Collins DL, Zijdenbos AP, Kollokian V, et al. Design and Construction of a Realistic Digital Brain Phantom. IEEE Trans Med Imaging. 1998;17(3):463-468.

Coupe P, Yger P, Prima S, Hellier P, Kervrann C, Barillot C. An optimized blockwise nonlocal means denoising filter for 3-D magnetic resonance imaging. IEEE Trans Med Imaging. 2008;27(4):425-441. doi: 10.1109/TMI.2007.906087.

Dabov, K., Foi, A., Katkovnik, V., Egiazarian, K.: Image denoising with block-matching and 3D filtering. Image Processing: Algorithms and Systems, Neural Networks, and Machine Learning. (2006).

Edwards AD, Arthurs OJ. Paediatric MRI under sedation: is it necessary? What is the evidence for the alternatives? Pediatr Radiol. 2011;41(11):1353-1364. doi: 10.1007/s00247-011-2147-7.

Feng X, Salerno M, Kramer CM, Meyer CH. Kalman filter techniques for accelerated Cartesian dynamic cardiac imaging. Magn Reson Med. 2013;69(5):1346-1356. doi: 10.1002/mrm.24375. PMCID: PMC3536913.

Feng X, Tustison N, Meyer CH. Brain Tumor Segmentation using an Ensemble of 3D U-Nets and Overall Survival Prediction using Radiomic Features. arXiv Preprints. 2018. arXiv:1812.01049.

Ghavhan GB, Babyn PS, Thomas B, Shroff MM, Haacke EM. Principles, techniques, and applications of T2*-based MR imaging and its special applications. Radiographics. 2009;29(5):1433-1449. doi: 10.1148/rg.295095034. PMCID: PMC2799958.

Glover GH, Li TQ, Ress D. Image-based method for retrospective correction of physiological motion effects in fMRI: Retroicor. Magn Reson Med. 2000;44(1):162-167.

Goodfellow IJ, Pouget-Abadie J, Mirza M, et al. Generative Adversarial Networks. arXiv Preprints. 2014. arXiv:1406.2661.

Griswold MA, Jakob PM, Heidemann RM, et al. Generalized autocalibrating partially parallel acquisitions (GRAPPA). Magn Reson Med. 2002;47(6):1202-1210.

Gudbjartsson H, Patz S. The Racian distribution of noisy MRI data. Magn Reson Med. 1995;34(6):910-914.

Harrison AP, Xu Z, Pourmorteza A, Bluemke DA, Mollura Dj. A multichannel block-matching denoising algorithm for spectral photon-counting CT images. Med Phys. 2017;44(6):2447-2452. doi: 10.1002/mp.12225.

Hartung MP, Grist TM, Francois CJ. Magnetic resonance angiography: current status and future directions. J Cardiovasc Magn Reson. 2011;13:19. doi: 10.1186/1532-429X-13-19. PMCID: PMC3060856.

Havsteen I, Ohlhues A, Madsen KH, et al. Are Movement Artifacts in Magnetic Resonance Imaging a Real Problem?—A Narrative Review. Front Neurol. 2017;8:232. doi: 10.3389/fneur.2017.00232. PMCID: PMC5447676.

Jiang D, Dou W, Vosters L, Xu X, Sun Y, Tan T. Denoising of 3D magnetic resonance images with multi-channel residual learning of convolutional neural network. Jpn J Radiol. 2018;36(9):566-574. doi: 10.1007/s11604-018-0758-8.

(56) References Cited

OTHER PUBLICATIONS

Kwan RK, Evans AC, Pike GB. An Extensible MRI Simulator for Post-Processing Evaluation. Visualization in Biomedical Computing (VBC'96). Lecture Notes in Computer Science, vol. 1131. Springer-Verlag, 1996. 135-140.

Kwan RK, Evans AC, Pike GB. MRI simulation-based evaluation of image-processing and classification methods. IEEE Trans Med Imaging. 1999;18(11):1085-1097.

Lustig M, Donoho D, Pauly JM. Sparse MRI: The application of compressed sensing for rapid MR imaging. Magn Reson Med. 2007;58(6):1182-1195.

Lustig M, Pauly JM. Spirit: Iterative self-consistent parallel imaging reconstruction from arbitrary k-space. Magn Reson Med. 2010;64(2):451-471. doi: 10.1002/mrm.22428. PMCID: PMC2925465.

Lyu Q, Yang C, Gao H, et al. Technical Note: Iterative megavoltage CT (MVCT) reconstruction using block-matching 3D-transform (BM3D) regularization. Med Phys. 2018;45(6):2603-2610. doi: 10.1002/mp.12916.

Maclaren J, Herbst M, Speck O, Zaitsev M. Prospective motion correction in brain imaging: a review. Magn Reson Med. 2013;69(3):621-636. doi: 10.1002/mrm.24314.

Macovski A. Noise in MRI. Magn Reson Med. 1996;36(3):494-497.

Maggioni M, Katkovnik V, Egiazarian K, Foi A. Nonlocal transform-domain filter for volumetric data denoising and reconstruction. IEEE Trans Image Process. 2013;22(1):119-133. doi: 10.1109/TIP.2012.2210725.

Manjon JV, Coupe P, Marti-Bonmati L, Collins DL, Robles M. Adaptive non-local means denoising of MR images with spatially varying noise levels. J Magn Reson Imaging. 2010;31(1):192-203. doi: 10.1002/jmri.22003.

McGibney G, Smith MR, Nichols ST, Crawley A. Quantitative evaluation of several partial Fourier reconstruction algorithms used in MRI. Magn Reson Med. 1993;30(1):51-59.

Patel, M.R., Klufas, R.A., Alberico, R.A., Edelman, R.R.: Half-fourier acquisition single-shot turbo spin-echo (HASTE) MR: comparison with fast spin-echo MR in diseases of the brain. American Journal of Neuroradiology. 18, 1635-1640 (1997).

Patrella JR, Provenzale JM. MR Perfusion imaging of the brain: techniques and applications. AJR Am J Roentgenol. 2000;175(1):207-219.

Pruessmann KP, Weiger M, Scheidegger MB, Boesiger P. Sense: sensitivity encoding for fast MRI. Magn Reson Med. 1999;42(5):952-962.

Saloner D. The AAPM/RSNA physics tutorial for residents. An introduction to MR angiography. Radiographics. 1995;15(2):453-465.

Schaefer PW, Grant PW, Gonzalez RG. Diffusion-weighted MR imaging of the brain. Radiology. 2000;217(2):331-345.

Shin HC, Roth HR, Gao M, et al. Deep Convolutional Neural Networks for Computer-Aided Detection: CNN Architectures, Dataset Characteristics and Transfer Learning. IEEE Trans Med Imaging. 2016;35(5):1285-1298. doi: 10.1109/TMI.2016.2528162. PMCID: PMC4890616.

Silva, Thalles, An intuitive introduction to Generative Adversarial Networks (GANs; https://www.freecodecamp.org/news/an-intuitive-introduction-to-generative-adversarial-networks-gans-7a2264a81394/ (accessed on Apr. 22, 2020).

Thunberg P, Zetterberg P. Noise distribution in SENSE- and GRAPPA-reconstructed images: a computer simulation study. Magn Reson Imaging. 2007;25(7):1089-1094.

Ulyanov, D., Vedaldi, A., Lempitsky, V.: Deep image prior. arXiv Preprints. (2017). 23 pages.

Vincent P, Larochelle H, Lajoie I, Bengio Y, Manzagol PA. Stacked Denoising Autoencoders: Learning Useful Representations in a Deep Network with a Local Denoising Criterion. J Mach Learn Res. 2010;11:3371-3408.

Wang Z, Bovid AC, Sheikh HR, Simoncelli EP. Image quality assessment: from error visibility to structural similarity. IEEE Trans Image Process. 2004;13(4):600-612. doi: 10.1109/TIP.2003.819861.

Zhang K, Zuo W, Chen Y, Meng D, Zhang L. Beyond a Gaussian Denoiser: Residual Learning of Deep CNN for Image Denoising. IEEE Trans Image Process. 2017;26(7):3142-3155. doi: 10.1109/TIP.2017.2662206.

Zhang X, Hou G, Ma J, et al. Denoising MR images using non-local means filter with combined patch and pixel similarity. PLoS One. 2014;9(6):e100240. doi: 10.1371/journal.pone.0100240.

Zhang X, Zhou X, Lin M, Sun J. ShuffleNet: An Extremely Efficient Convolutional Neural Network for Mobile Devices. arXiv Preprints. 2017. arXiv:1707.01083.

Zhao L, Fielden SW, Feng X, Wintermark M, Muger JP 3rd, Meyer CH. Rapid 3D dynamic arterial spin labeling with a sparse model-based image reconstruction. Neuroimage. 2015;205-216. doi: 10.1016/j.neuroimage.2015.07.018. PMCID: PMC4615585.

Zhao T, Hoffman J, McNitt-Gray M, Ruan D. Ultra-low-dose CT image denoising using modified BM3D scheme tailored to data statistics. Med Phys. 2019;46(1):190-198. doi: 10.1002/mp.13252.

International Search Report and Written Opinion issued in International Application No. PCT/US2020/029566, dated Jul. 2, 2020, 9 pages.

* cited by examiner

DENOISING MAGNETIC RESONANCE IMAGES USING UNSUPERVISED DEEP CONVOLUTIONAL NEURAL NETWORKS

CROSS-REFERENCE TO RELATED APPLICATION

This Application is a national phase entry under 35 U.S.C. § 371 of International Application No. PCT/US2020/029866, filed on Apr. 24, 2020, which claims priority to and benefit of U.S. Provisional Patent Application Ser. No. 62/837,874 entitled "Unsupervised System and Method for MR Imaging Denoising and Super-Resolution" filed Apr. 24, 2019, both of which are hereby incorporated by reference herein in their entireties as if fully set forth below.

FIELD

The present disclosure relates to systems and methods for denoising magnetic resonance images using unsupervised deep convolutional neural networks.

BACKGROUND

Magnetic resonance imaging (MRI) is an important diagnostic tool for various conditions, including brain conditions. Because of the good soft tissue contrast, non-invasiveness and lack of ionizing radiation of MRI, it is widely used as a diagnostic tool for brain conditions including stroke, tumors, multiple sclerosis (MS), hemorrhage, blood vessel issues, and neurodegenerative diseases. A clinical protocol often includes pre- and post-contrast T1, T2, fluid-attenuated inversion recovery (FLAIR), proton density (PD) and diffusion weighted images (DWI). Other advanced sequences such as magnetic resonance angiography (MRA) and perfusion MRI using dynamic susceptibility contrast (DSC) and arterial spin labeling (ASL) are also used for specific conditions. Although different contrasts provide enriched diagnostic information, the challenges are prolonged scan time and increased artifacts due to motion [1A], especially for pediatric patients who have trouble holding still during the scan and thus sedation/anesthesia is often needed for a successful exam [2A].

Extensive studies have been performed to accelerate MRI and reduce motion artifacts with the application to the brain and other regions of the body. Most studies have focused on improving the data acquisition strategies, such as using partial Fourier [3A], parallel imaging [4A-6A] and compressed sensing [7A] to reduce the number of acquired k-space lines without introducing aliasing, many of which are already widely used in clinical protocols. Retrospective [8A] and prospective [9A] motion correction methods have also been developed to specifically reduce the artifacts. However, these acquisition strategies often introduce trade-offs among speed, resolution and image quality, which is typically evaluated by the real or apparent signal-to-noise ratio (SNR), so that further acceleration of the scan can lead to reduced SNR and/or spatial resolution. In clinical practice, these aspects are balanced to yield a standard protocol. Denoising algorithms, which are applied during post-processing, can increase SNR without introducing any negative effects to the acquisition process and thus have the potential to shift the balance towards more aggressive acceleration and compensate for the reduced SNR in the original images.

Denoising algorithms can improve signal-to-noise ratio (SNR) without prolonging the scan time. Filter-based denoising methods, such as non-local means (NLM) and block-matching and 3D filtering (BM3D), suffer when dealing with small lesion regions and non-uniform noise patterns due to parallel imaging and B1 inhomogeneity from multiple coils. Recently deep convolutional neural networks have been developed for denoising; however, they require high-quality training data, which is difficult to obtain in practice. The networks are usually trained with the noise-corrupted images as the input and the noise-reduced/noise-free images as the output. The input can be simulated from the output images by adding noise at one or multiple levels with the desired distribution or from actual images acquired with low SNR. The DCNN can then learn from the "examples" to achieve good denoising when the new images are similar to those in the training dataset. In addition to its improved performance, the DCNN is also much faster to run as only one forward pass is required once it is trained In clinical practice, a clear MRI with high signal to noise ratio (SNR) is usually favored for accurate lesion detection and diagnosis. Improving the SNR of MRI can be achieved by changing the parameters of acquisition sequences such as using more averages and lower bandwidth; however, this often comes with prolonged scan time. On the contrary, improving SNR with denoising algorithms during post-processing would not change the scan process and therefore is an attractive alternative option. Most of the denoising algorithms can be categorized as traditional filter-based methods and learning-based methods. Filter-based methods, including non-local means (NLM) [1] and block-matching and 3D filtering (BM3D) [2], often rely on repetitive structures in the images so that local or global averages can be applied to reduce noise. The main disadvantages of these methods include the following: 1) a large number of similar structures need to exist in the input images to achieve good performance, which can become problematic for fine structures and pathological regions as fewer such blocks exist; and 2) the performance is highly dependent on algorithm parameters, which can vary significantly for different sequences and noise levels, especially when advanced image acquisition methods, such as parallel imaging with multiple receiver coils, are used, as the noise distribution is much more complicated.

Now with reference to prior art FIG. 3, a U-Net is a convolutional neural network architecture. U-Nets may be effective for tasks where the output is of similar size as the input and the output needs a similar level of spatial resolution. This makes a U-Net effective for super resolution image processing. To perform classification using a convolutional neural network the image is down-sampled into one or more classifications using a series of stride two convolutions reducing the grid size each time. To be able to output a generated image of the same size as the input, or larger, an up-sampling path is used to increase the grid size.

The up-sampling/decoder path may include several transposed convolutions can be used, where each transposed convolution adds pixels between and around the existing pixels. Each up-sample in the decoder/up-sampling part of the network can add pixels around the existing pixels and also between the existing pixels to eventually reach the desired resolution. Replication padding is then performed to provide an extra pixel around the image. Then average pooling can be performed to extract features smoothly. After new pixels are added, the subsequent convolutions can improve the level of detail as the path continues through the decoder path of the network an upscaling step increases the dimensions of the image.

The 3D UNet was originally proposed by Cicek et al. [8] for automatic segmentation of Xenopus (a highly aquatic frog) kidney. It has an encoder-decoder style architecture with skip connections between corresponding layers in encoding and decoding paths. This architecture is very popular for medical image segmentation. FIG. 3 shows the block representation of 3D UNet architecture.

Each convolutional block has two convolutions followed by max pooling. Every convolution is immediately followed by a rectified linear unit (ReLU) activation and batch normalization layer. Each deconvolutional block consists of two convolutions followed by a deconvolution to regain spatial dimension. Moreover, there are skip connections from the encoding path to decoding path at corresponding spatial dimensions. These are shown by green arrows. The very final convolution generates a three-dimensional feature map and is followed by activation in order to obtain a pseudo-random probability distribution at each pixel representing its class membership.

Deep convolutional neural networks (DCNN) with various architectures have yielded performance superior to traditional methods [3]. These networks are usually trained with the noise-corrupted images as the input and the noise-free images as the target output. The DCNN can then learn from the "examples" to achieve good denoising when the new images are similar to those in the training data. However, a disadvantage is the sole reliance on the training data, or good "examples", which are difficult to obtain in practice. Simulating low SNR images by adding noise often uses a very simplified noise model with a spatially uniform Gaussian or Rician distribution, and thus cannot represent more complicated cases with non-uniform noise from multiple coils. Acquiring paired low and high SNR images can overcome this issue but suffers from any mismatches between the two acquisitions. As the number of training examples from each sequence type may need to be large and diverse to obtain good performance, the data collection can be challenging and expensive. Furthermore, if a sequence type is not in the training set, it is doubtful whether the model can generalize to this sequence. In order to solve the problem of over-dependence on training data, an unsupervised deep convolutional neural network (U-DCNN) that does not require training from "examples" but relies on different characteristics of the network against signal and noise was recently proposed and produced compelling results on denoising natural images [4].

Now with reference to FIG. 4, adapted from Silva [9] generative adversarial networks (GANs) include a generator neural network and a discriminator neural network. The discriminator neural network is configured to determine whether an input image is a real image or a synthetic image. Real "ground truth" images are input into the discriminator neural network along with synthetic images created by the generator network. The generator neural network is configured alter its output in order to increase the chance that the images produced by the generator neural network will be categorized as real images by the discriminator neural network. Similarly, the discriminator neural network is configured to alter its behavior to more accurately identify the synthetic images in response. Therefore both the generator neural network and discriminator neural network are in a feedback loop with each other.

Among other needs, there is a need for a U-DCNN that requires no training data for MRI denoising but is instead based on the structure characteristic itself. It is with respect to these and other considerations that the various embodiments described below are presented.

SUMMARY

In one aspect, the present disclosure relates to a computer-implemented method of denoising a magnetic resonance (MR) image which, in one embodiment, includes: acquiring magnetic resonance (MR) image data of an area of interest of a subject, wherein the image data comprises noisy input images, and wherein the noisy input images comprise noise data and noise free image data. The method also includes, for each of the noisy input images: running iterations of a converging sequence in an unsupervised deep convolutional neural network (U-DCNN); in each iteration, updating parameter settings used in calculating a series of image feature sets with the U-DCNN, the image feature sets predicting an output image; and terminating the converging sequence of the U-DCNN before the feature sets predict a respective output image that replicates all of the noise data from the noisy input image. The method also includes outputting, based on a selected feature set, a denoised MR image of the area of interest of the subject.

In some embodiments, the method includes terminating the converging sequence at a selected final set of the parameter settings calculated during the iterations of the U-DCNN.

In some embodiments, the method includes randomly assigning first values to the weights and biases in the parameter settings.

In some embodiments, the U-DCNN includes encoding layers, decoding layers and skip layers with respective intermediate outputs, and the method also includes processing a higher percentage of noise free image data through the intermediate layers and a lower percentage of noise data through the intermediate layers prior to the step of terminating the converging sequence.

In some embodiments, the method includes constraining the iterations by structuring the U-DCNN with two layers of encoding and two layers of decoding.

In some embodiments, the method includes calculating a series of skip layer intermediate outputs using respective encoding layer intermediate outputs from each encoding layer; and concatenating respective skip layer intermediate outputs with a respective decoding layer intermediate output.

In some embodiments, the method includes applying a Gaussian filter to respective noisy input images prior to running iterations of the U-DCNN.

In some embodiments, the method includes down sampling the respective noisy images by a selected factor prior to running iterations of the U-DCNN.

In some embodiments, the acquiring the MR image data comprises multi-slice or 3D acquisition, wherein the denoising incorporates spatial information along the through-plane dimension.

In some embodiments, the U-DCNN is configured for 3D convolution, wherein the denoising comprises reconstructing a first stack of the acquired slices together, and reconstructing a second stack of the acquired slices together upon denoising the first stack of the acquired slices.

In some embodiments, the area of interest of the subject is at least a part of the brain of the subject.

In some embodiments, the method also includes acquiring high signal to noise ratio (SNR) MR image data in selected acquisition sequences, concatenating the high SNR image data with the noise data and the noise free image data to form the noisy input image.

In some embodiments, the denoising of the MR image is performed as part of magnetic resonance angiography, diffusion MRI, or perfusion MRI.

In some embodiments, the high SNR image data comprises MR image data acquired in T1, T2, or proton density (PD) sequences.

In another aspect, the present disclosure relates to a system for denoising a magnetic resonance (MR) image. In one embodiment, the system includes: one or more processors; and a memory device coupled to the one or more processors and storing instructions which, when executed by the one or more processors, cause the system to perform functions that include: acquiring magnetic resonance (MR) image data of an area of interest of a subject, wherein the image data comprises noisy input images, and wherein the noisy input images comprise noise data and noise free image data. The functions performed by the system also include, for each of the noisy input images: running iterations of a converging sequence in an unsupervised deep convolutional neural network (U-DCNN); in each iteration, updating parameter settings used in calculating a series of image feature sets with the U-DCNN, the image feature sets predicting an output image; terminating the converging sequence of the U-DCNN before the feature sets predict a respective output image that replicates all of the noise data from the noisy input image; and outputting, for each iteration, an updated compilation of denoised MR image data of the area of interest of the subject.

In some embodiments, the system also includes a display configured to provide a view of the updated compilation of denoised MR image data for each iteration.

In some embodiments, the system also includes a user interface configured to receive a selected number of iterations at which the computer terminates the converging sequence.

In some embodiments, the system also includes a control system configured to track a number of iterations completed for each view.

In some embodiments, the noise data comprises non-uniform noise originating from coils used in multi-band MR image acquisitions.

In some embodiments, a plurality of the noisy input images are previously calculated as diagnostic compilations of acquired image data from parallel channels.

In some embodiments, the diagnostic compilations comprise calculated images showing at least one of the subject's apparent diffusion coefficient (ADC), cerebral blood flow (CBF) and cerebral blood volume (CBV).

In yet another aspect, the present disclosure relates to a non-transitory computer-readable medium storing instructions thereon which, when executed by one or more processors, cause a computer to perform functions for denoising a magnetic resonance (MR) image. The functions performed for denoising the MR image include: acquiring magnetic resonance (MR) image data of an area of interest of a subject, wherein the image data comprises noisy input images, and wherein the noisy input images comprise noise data and noise free image data; and, for each of the noisy input images: running iterations of a converging sequence in an unsupervised deep convolutional neural network (U-DCNN); in each iteration, updating parameter settings used in calculating a series of image feature sets with the U-DCNN, the image feature sets predicting an output image; and terminating the converging sequence of the U-DCNN before the feature sets predict a respective output image that replicates all of the noise data from the noisy input image. The functions performed for denoising the MR image also include outputting, based on a selected feature set, a denoised MR image of the area of interest of the subject.

Other aspects and features according to the example embodiments of the present disclosure will become apparent to those of ordinary skill in the art, upon reviewing the following detailed description in conjunction with the accompanying figures.

BRIEF DESCRIPTION OF THE DRAWINGS

Reference will now be made to the accompanying drawings, which are not necessarily drawn to scale.

DETAILED DESCRIPTION

Figure 1:
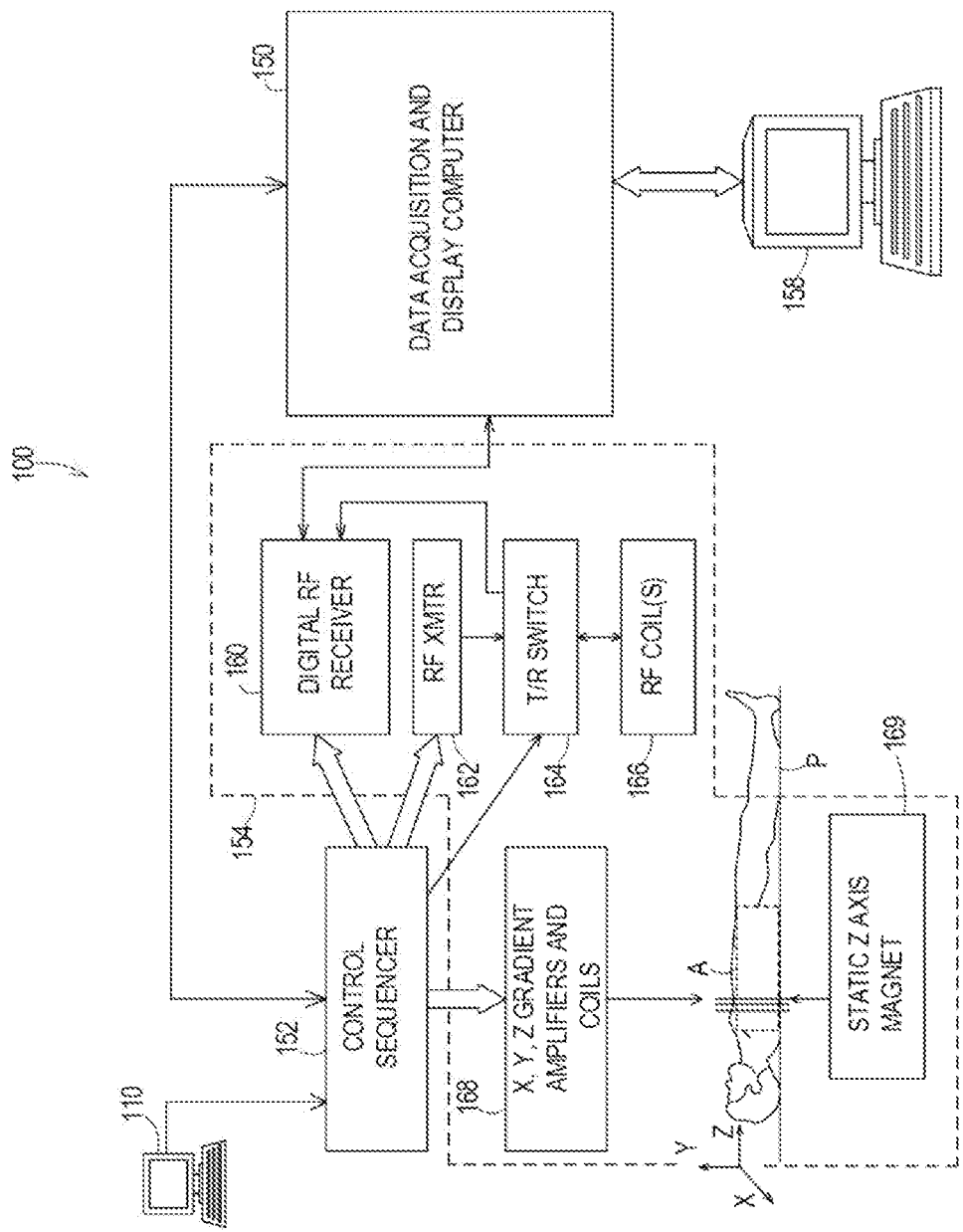
FIG. 1 is a system diagram illustrating an operating environment capable of implementing aspects of the present disclosure.

Although example embodiments of the present disclosure are explained in detail herein, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

It must also be noted that, as used in the specification and the appended claims, the singular forms "a," "an" and "the" include plural referents unless the context clearly dictates otherwise. Ranges may be expressed herein as from "about" or "approximately" one particular value and/or to "about" or "approximately" another particular value. When such a range is expressed, other exemplary embodiments include from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the present disclosure. Similarly, it is also to be understood that the mention of one or more components in a device or system does not preclude the presence of additional components or intervening components between those components expressly identified.

As discussed herein, a "subject" (or "patient") may be any applicable human, animal, or other organism, living or dead, or other biological or molecular structure or chemical environment, and may relate to particular components of the subject, for instance specific organs, tissues, or fluids of a subject, may be in a particular location of the subject, referred to herein as an "area of interest" or a "region of interest."

Some references, which may include various patents, patent applications, and publications, are cited in reference lists and discussed in the disclosure provided herein. The citation and/or discussion of such references is provided merely to clarify the description of the present disclosure and is not an admission that any such reference is "prior art" to any aspects of the present disclosure described herein. In terms of notation, "[n]" corresponds to the $n^{th}$ reference in the list. For example, "[3]" refers to the $3^{rd}$ reference in the list, namely Zhang, K., Zuo, W., Chen, Y., Meng, D., Zhang, L.: Beyond a Gaussian Denoiser: Residual Learning of Deep CNN for Image Denoising. IEEE Transactions on Image Processing. 26, 3142-3155 (2017). All references cited and discussed in this specification are incorporated herein by reference in their entireties and to the same extent as if each reference was individually incorporated by reference.

A detailed description of aspects of the present disclosure, in accordance with various example embodiments, will now be provided with reference to the accompanying drawings. The drawings form a part hereof and show, by way of illustration, specific embodiments and examples. In referring to the drawings, like numerals represent like elements throughout the several figures. Some experimental data are presented herein for purposes of illustration and should not be construed as limiting the scope of the present disclosure in any way or excluding any alternative or additional embodiments.

FIG. 1 is a system diagram illustrating an operating environment capable of implementing aspects of the present disclosure in accordance with one or more example embodiments. FIG. 1 illustrates an example of a magnetic resonance imaging (MRI) system 100, including a data acquisition and display computer 150 coupled to an operator console 110, an MRI real-time control sequencer 152, and an MRI subsystem 154. The MRI subsystem 154 may include XYZ magnetic gradient coils and associated amplifiers 168, a static Z-axis magnet 169, a digital RF transmitter 162, a digital RF receiver 160, a transmit/receive switch 164, and RF coil(s) 166. The MRI subsystem 154 may be controlled in real time by control sequencer 152 to generate magnetic and radio frequency fields that stimulate magnetic resonance phenomena in a living subject, patient P, to be imaged. A contrast-enhanced image of an area of interest A of the patient P may be shown on display 158. The display 158 may be implemented through a variety of output interfaces, including a monitor, printer, or data storage.

The area of interest "A" corresponds to a region associated with one or more physiological activities in patient "P". The area of interest shown in the example embodiment of FIG. 1 corresponds to a chest region of patient "P", but the area of interest for purposes of implementing aspects of the disclosure presented herein is not limited to the chest area. It should be recognized and appreciated that the area of interest can be one or more of a brain region, heart region, and upper or lower limb regions of the patient "P", for example.

It should be appreciated that any number and type of computer-based medical imaging systems or components, including various types of commercially available medical imaging systems and components, may be used to practice certain aspects of the present disclosure. Systems as described herein with respect to example embodiments are not intended to be specifically limited to magnetic resonance imaging (MRI) implementations or the particular system shown in FIG. 1.

One or more data acquisition or data collection steps as described herein in accordance with one or more embodiments may include acquiring, collecting, receiving, or otherwise obtaining data such as imaging data corresponding to an area of interest. By way of example, data acquisition or collection may include acquiring data via a data acquisition device, receiving data from an on-site or off-site data acquisition device or from another data collection, storage, or processing device. Similarly, data acquisition or data collection devices of a system in accordance with one or more embodiments of the present disclosure may include any device configured to acquire, collect, or otherwise obtain data, or to receive data from a data acquisition device within the system, an independent data acquisition device located on-site or off-site, or another data collection, storage, or processing device.

Figure 2:
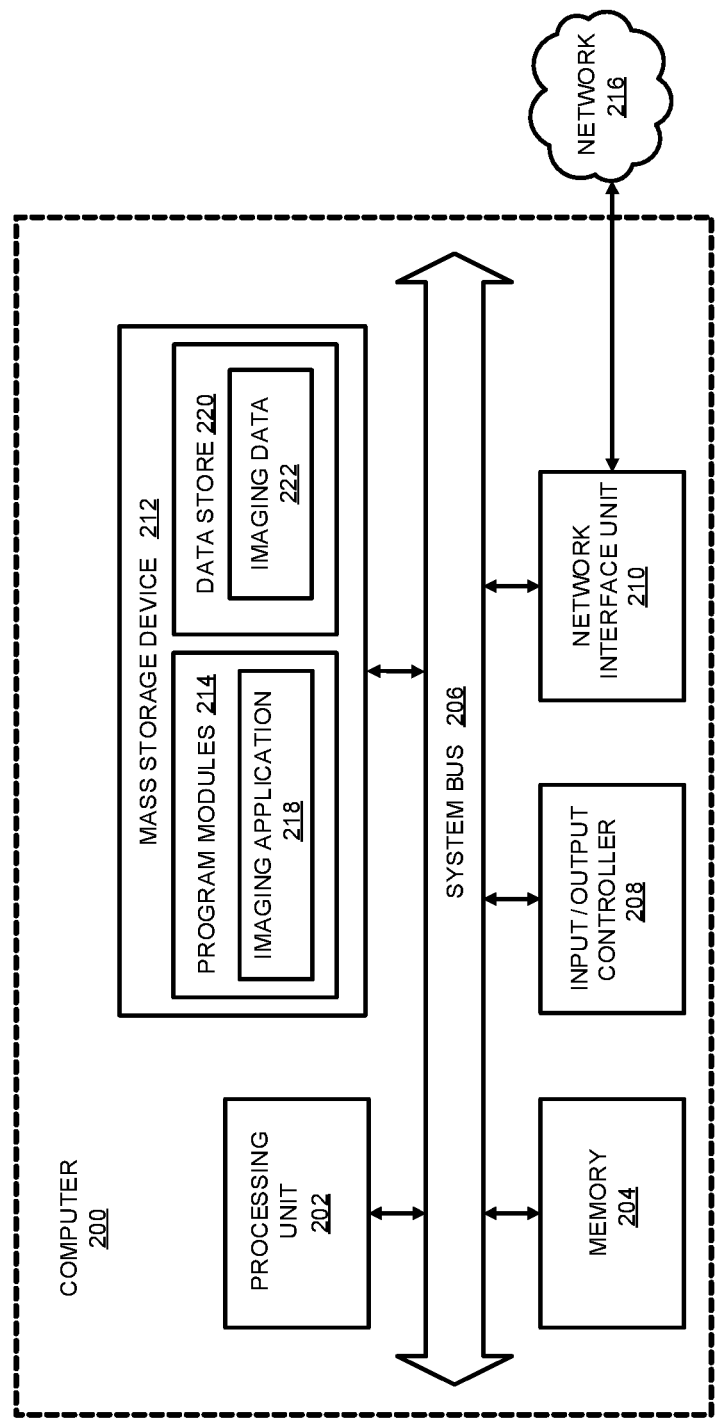
FIG. 2 is a computer architecture diagram showing a general computing system capable of implementing aspects of the present disclosure.

FIG. 2 is a computer architecture diagram showing a general computing system capable of implementing aspects of the present disclosure in accordance with one or more embodiments described herein. A computer 200 may be configured to perform one or more functions associated with embodiments of this disclosure. For example, the computer 200 may be configured to perform operations for denoising MR images as described herein with respect to certain embodiments. It should be appreciated that the computer 200 may be implemented within a single computing device or a computing system formed with multiple connected computing devices. The computer 200 may be configured to perform various distributed computing tasks, which may distribute processing and/or storage resources among the multiple devices. The data acquisition and display computer 150 and/or operator console 110 of the system shown in FIG. 1 may include one or more systems and components of the computer 200.

As shown, the computer 200 includes a processing unit 202 ("CPU"), a system memory 204, and a system bus 206 that couples the memory 204 to the CPU 202. The computer 200 further includes a mass storage device 212 for storing program modules 214. The program modules 214 may be operable to perform one or more functions associated with embodiments of method as illustrated in one or more of the figures of this disclosure, for example to cause the computer 200 to perform operations of the present disclosure as described below. The program modules 214 may include an imaging application 218 for performing data acquisition functions as described herein, for example to receive image data corresponding to magnetic resonance imaging of an area of interest. The computer 200 can include a data store 220 for storing data that may include imaging-related data 222 such as acquired image data, and a modeling data store 224 for storing image modeling data, or other various types of data utilized in practicing aspects of the present disclosure.

The mass storage device 212 is connected to the CPU 202 through a mass storage controller (not shown) connected to the bus 206. The mass storage device 212 and its associated computer-storage media provide non-volatile storage for the computer 200. Although the description of computer-storage media contained herein refers to a mass storage device, such as a hard disk or CD-ROM drive, it should be appreciated by those skilled in the art that computer-storage media can be any available computer storage media that can be accessed by the computer 200.

By way of example, and not limitation, computer-storage media (also referred to herein as a "computer-readable storage medium" or "computer-readable storage media") may include volatile and non-volatile, removable and non-removable media implemented in any method or technology for storage of information such as computer-storage instructions, data structures, program modules, or other data. For example, computer storage media includes, but is not limited to, RAM, ROM, EPROM, EEPROM, flash memory or other solid state memory technology, CD-ROM, digital versatile disks ("DVD"), HD-DVD, BLU-RAY, or other optical storage, magnetic cassettes, magnetic tape, magnetic disk storage or other magnetic storage devices, or any other medium which can be used to store the desired information and which can be accessed by the computer 200. Transitory signals are not "computer-storage media", "computer-readable storage medium" or "computer-readable storage media" as described herein.

According to various embodiments, the computer 200 may operate in a networked environment using connections to other local or remote computers through a network 216 via a network interface unit 210 connected to the bus 206. The network interface unit 210 may facilitate connection of the computing device inputs and outputs to one or more suitable networks and/or connections such as a local area network (LAN), a wide area network (WAN), the Internet, a cellular network, a radio frequency network, a Bluetooth-enabled network, a Wi-Fi enabled network, a satellite-based network, or other wired and/or wireless networks for communication with external devices and/or systems. The computer 200 may also include an input/output controller 208 for receiving and processing input from a number of input devices. Input devices may include one or more of keyboards, mice, stylus, touchscreens, microphones, audio capturing devices, or image/video capturing devices. An end user may utilize such input devices to interact with a user interface, for example a graphical user interface, for managing various functions performed by the computer 200.

The bus 206 may enable the processing unit 202 to read code and/or data to/from the mass storage device 212 or other computer-storage media. The computer-storage media may represent apparatus in the form of storage elements that are implemented using any suitable technology, including but not limited to semiconductors, magnetic materials, optics, or the like. The computer-storage media may represent memory components, whether characterized as RAM, ROM, flash, or other types of technology. The computer-storage media may also represent secondary storage, whether implemented as hard drives or otherwise. Hard drive implementations may be characterized as solid state or may include rotating media storing magnetically-encoded information. The program modules 214, which include the imaging application 218, may include instructions that, when loaded into the processing unit 202 and executed, cause the computer 200 to provide functions associated with embodiments illustrated herein. The program modules 214 may also provide various tools or techniques by which the computer 200 may participate within the overall systems or operating environments using the components, flows, and data structures discussed throughout this description.

In general, the program modules 214 may, when loaded into the processing unit 202 and executed, transform the processing unit 202 and the overall computer 200 from a general-purpose computing system into a special-purpose computing system. The processing unit 202 may be constructed from any number of transistors or other discrete circuit elements, which may individually or collectively assume any number of states. More specifically, the processing unit 202 may operate as a finite-state machine, in response to executable instructions contained within the program modules 214. These computer-executable instructions may transform the processing unit 202 by specifying how the processing unit 202 transitions between states, thereby transforming the transistors or other discrete hardware elements constituting the processing unit 202.

Encoding the program modules 214 may also transform the physical structure of the computer-storage media. The specific transformation of physical structure may depend on various factors, in different implementations of this description. Examples of such factors may include but are not limited to the technology used to implement the computer-storage media, whether the computer storage media are characterized as primary or secondary storage, and the like. For example, if the computer-storage media are implemented as semiconductor-based memory, the program modules 214 may transform the physical state of the semiconductor memory, when the software is encoded therein. For example, the program modules 214 may transform the state of transistors, capacitors, or other discrete circuit elements constituting the semiconductor memory.

As another example, the computer-storage media may be implemented using magnetic or optical technology. In such implementations, the program modules 214 may transform the physical state of magnetic or optical media, when the software is encoded therein. These transformations may include altering the magnetic characteristics of particular locations within given magnetic media. These transformations may also include altering the physical features or characteristics of particular locations within given optical media, to change the optical characteristics of those locations. Other transformations of physical media are possible without departing from the scope of the present description, with the foregoing examples provided only to facilitate this discussion.

Commercially available medical imaging systems and components, may be used to practice certain aspects of the present disclosure. These commercially available imaging systems include 1.5 T and 3 T MRI scanners.

Figure 3:
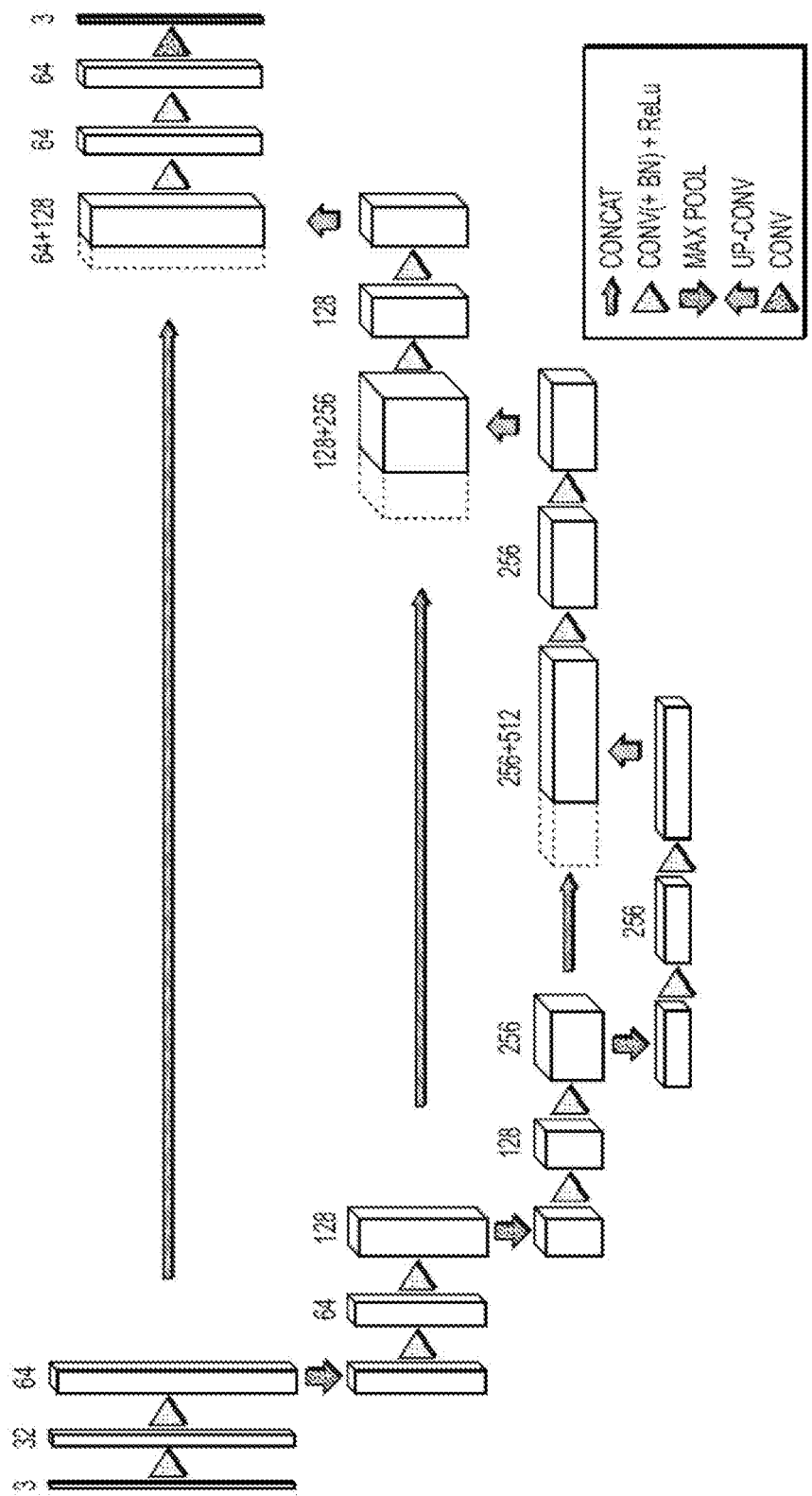
FIG. 3 is a PRIOR ART schematic that illustrates a conventional U-Net.

With reference to background FIG. 3, a schematic of a U-Net is shown. The boxes represent feature maps, and the number of channels is labelled on each feature map. Neural network operations set forth in the legend of FIG. 3, including convolution and max pooling, are represented by arrows between each feature map.

Figure 4:
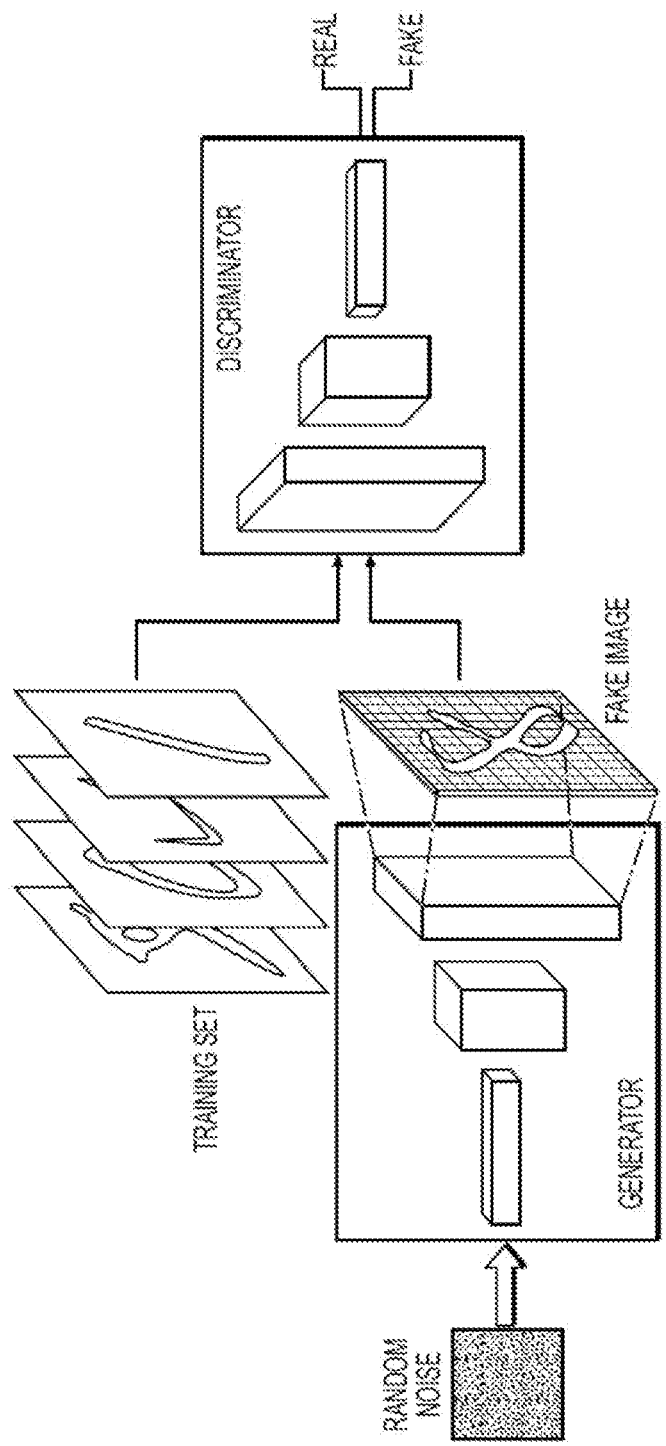
FIG. 4 is a PRIOR ART schematic that illustrates a conventional Generative Adversarial Network (GAN) including a generator, a discriminator, and a training set.

With reference to background FIG. 4, a schematic of a generative adversarial neural network is shown. The generator neural network produces a "fake image" based on random noise input into the generator. The fake image and a training set of real images are input into the discriminator neural network. The discriminator neural network is configured to determine whether the input image is a "fake" image produced by the generator neural network. Based on feedback from the discriminator, the generator neural network is configured to alter its output in order to decrease the likelihood that the discriminator will determine that the fake image is a fake image.

Some embodiments of the present disclosure include an Unsupervised Deep Convolutional Neural Network (U-DCNN) 600 (FIG. 6) with structural improvements specifically for denoising MRIs. Some embodiments of the present disclosure only require a noisy MRI to be denoised as the input and functions as a traditional filter so that no simulated or acquired high-quality training data is needed. Instead of relying on averaging, the U-DCNN* 600 uses a DCNN structure and therefore is more robust in denoising performances and maintaining fine structures, especially for non-uniform noise in a clinical MR image. Embodiments of the present disclosure include different network designs with a variety of input images, network depths, and skip-connections.

The structure and hyper-parameters of the U-DCNN 600 can be optimized for brain MRI. Embodiments of the present disclosure have been validated with a simulated brain MRI dataset at various noise levels and an acquired dataset with parallel imaging. Comparisons with non-local means (NLM) and block-matching and 3D filtering (BM3D) were made, demonstrating a superior and more robust performance over the traditional filter-based methods, especially on the acquired MRI with non-uniform noise.

According to some embodiments of the present disclosure, the U-DCNN 600 is a deep generator network, which can be regarded as a highly non-linear parametric function $x = f_\theta(z)$ that maps an input z to a denoised image x. The parameters $\theta$ can be comprised of the weights and bias of the network's filtering operations including convolutions, up-sampling and non-linear activation functions. The final set of parameters can be obtained using an optimizer such as gradient descent and a loss function, starting from a random parameter initialization. As discussed in [4], such a network structure has high impedance to noise and low impedance to signal. In other words, when generating x, it is much easier to obtain the parameter set for an image than random noise, as the patterns in an image can make the generation process more convenient. For natural images, U-DCNN 600 has demonstrated a faster convergence towards naturally-looking images than corrupted noisy images [4].

Figure 5:
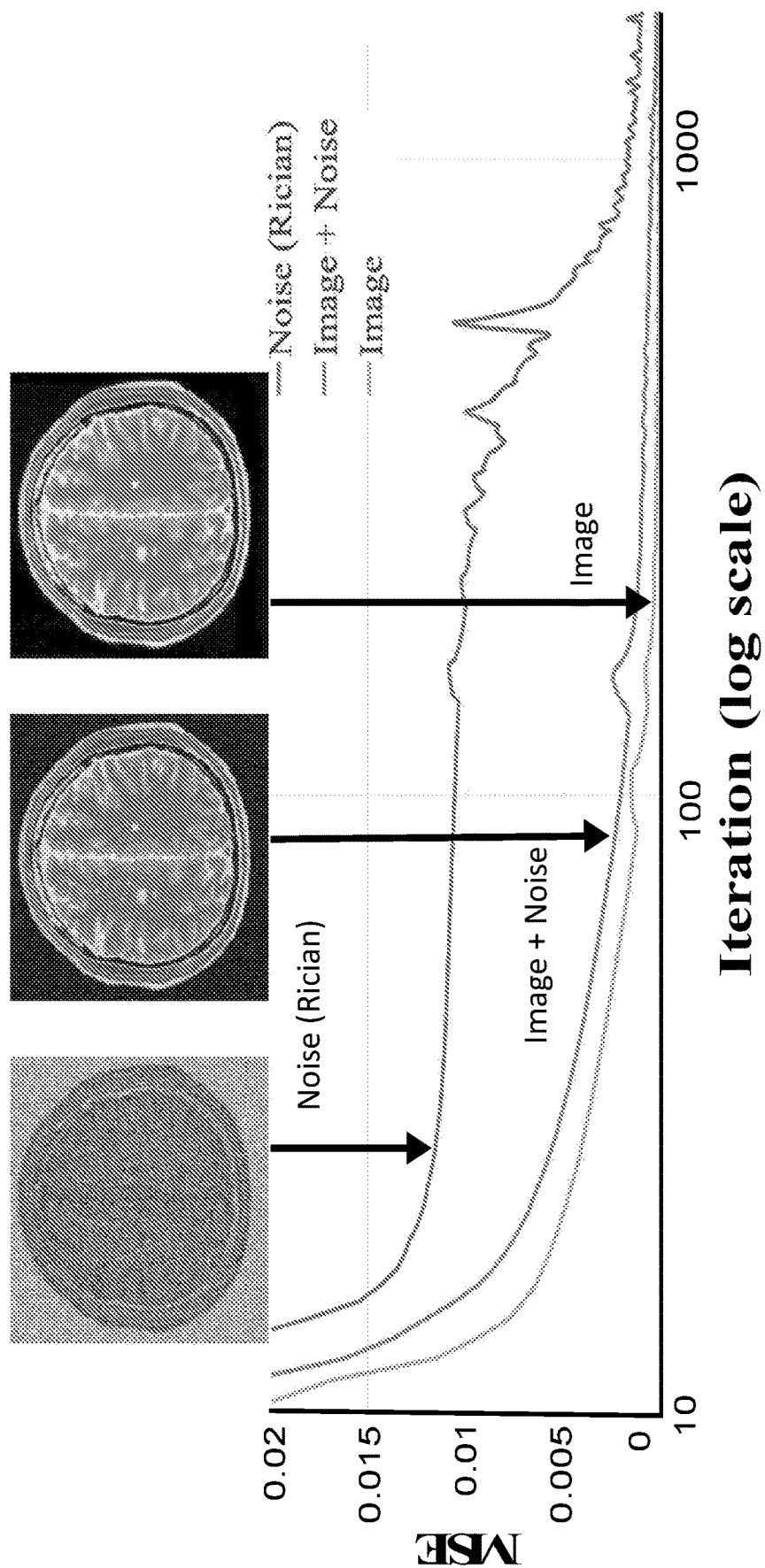
FIG. 5 illustrates learning curves for a reconstruction task using a noise-free MR image, the same image plus Rician noise, and the Rician noise alone. In this reconstruction task, the noise-free image results in the fastest convergence, whereas noise is the slowest.

The denoising performance can be different between MRI and natural images because: 1) MRI has different image characteristics, 2) the fine structural details, such as small lesions, matter more in MRI, and 3) MRI noise is usually more complex than the uniform Gaussian noise on natural images, especially with multiple receiver coils. In order to study the denoising capability of U-DCNN on MRI, the generation process for the synthetic noise-free brain MRI, Rician noise itself and noisy MRI using the mean squared error (MSE) between the output of U-DCNN and the specific target was examined. As shown in FIG. 5, it is apparent that the convergence speed for noise-free MRI is the fastest and for Rician noise is the slowest. Therefore, in some embodiments of the present disclosure, the number of iterations in the learning process can be limited to obtain a denoised MR image 705 from the U-DCNN 600 by suppressing noise.

Figure 6:
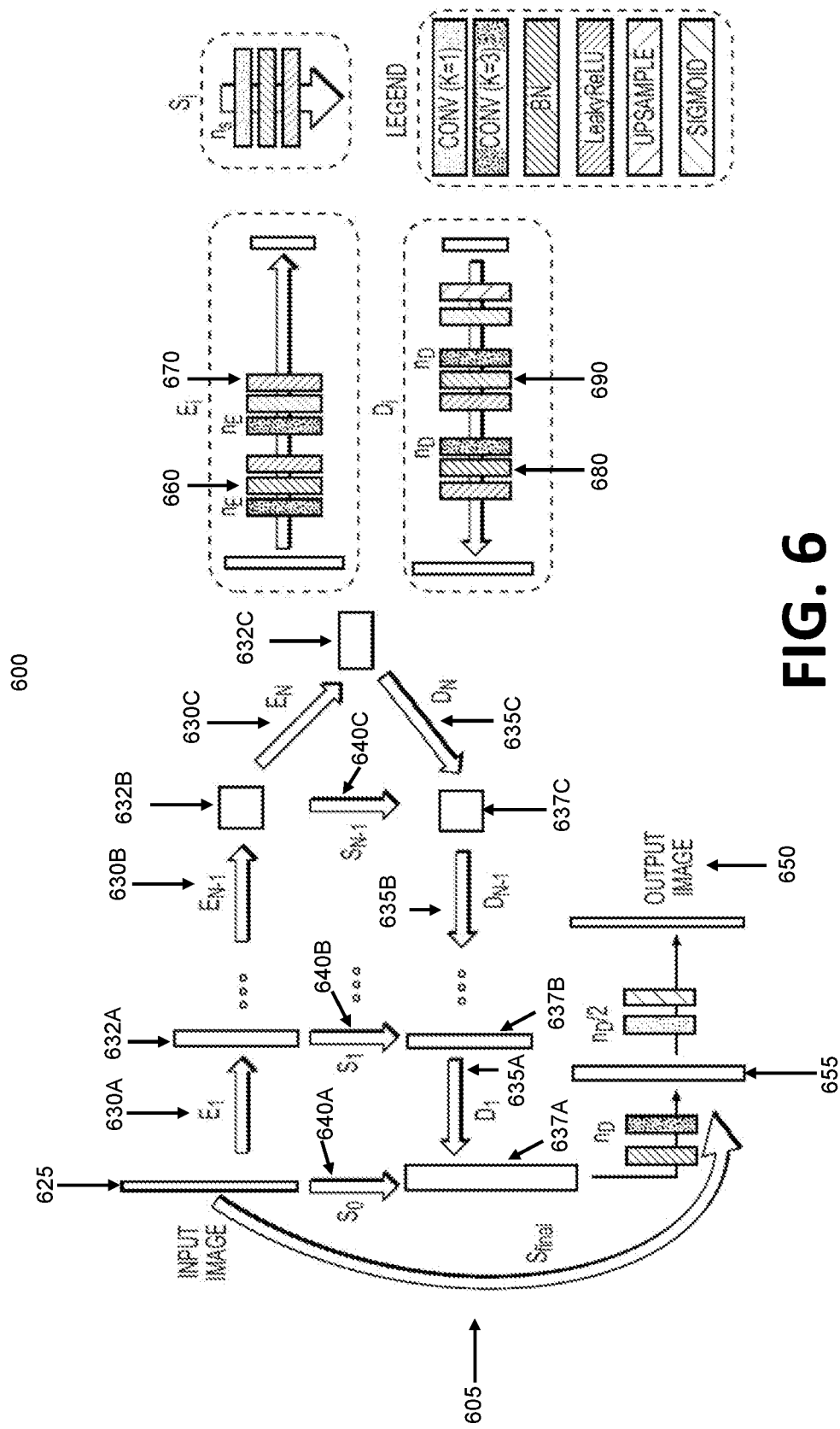
FIG. 6 illustrates the network structure for an embodiment of an Unsupervised Deep Convolutional Neural Network (U-DCNN) with N layers. The values nE, nD and nS correspond to the number of features for the encoding, decoding and skip-connections respectively. K refers to kernel size.

As depicted in FIG. 6, embodiments of the present disclosure include a U-Net-like architecture. The encoding path can capture image characteristics at various resolutions and the decoding path can generate the output image 650 based on those condensed image characteristics. For each denoising case, the network 600 can be given an input image 625 and fitted to the raw noisy MRI, which can be the target image used for calculating network loss.

Compared with random noise, an image carries more information and has a much better-defined pattern. DCNN is better at capturing the patterns than the random noise and thus can generate the image much faster than noise from a given input, so DCNN can be used to suppress the noise level by stopping early in the reconstruction process of the noisy image. DCNN structures are effective for capturing both low-level and high-level image characteristics and the structure of stacked denoising auto-encoders. Embodiments of the present disclosure implement a denoising algorithm that relies on the differences in convergence speed of the DCNN when generating true images and random noise [24A]. Using a DCNN generator with a similar network structure as in the generative adversarial network [25A], the true image converges much faster and is easier to generate than noise from a given input; therefore, when the generation iterations are stopped early, the noise level in the noisy image can be effectively suppressed according to some embodiments of the present disclosure. As shown in [24A], it is advantageous over NLM and BM3D in maintaining the fine structures while reducing noise in natural images.

According to some embodiments of the present disclosure, the method for denoising images includes acquiring MR image data 160 of the area of interest A of the subject P and processing that data using a U-DCNN 600 to remove the noise. The area of interest A may include at least a part of the brain of the subject P or patient. Embodiments of the present disclosure may be used to denoise images produced by magnetic resonance angiography, diffusion MRI, perfusion MRI, or other medical imaging techniques. The noise data 710 can comprise non-uniform noise originating from coils 168 used in multi-band MR image acquisitions. The noisy input images 625 input to the system can be previously calculated as diagnostic compilations of acquired image data from parallel channels, and the diagnostic compilations can include calculated images showing the subject P or patient's apparent diffusion coefficient, cerebral blood flow and cerebral blood volume. The high SNR image data can include MR image data 160 acquired during different MRI sequences, including the T1, T2, and PD sequences.

Figure 7:
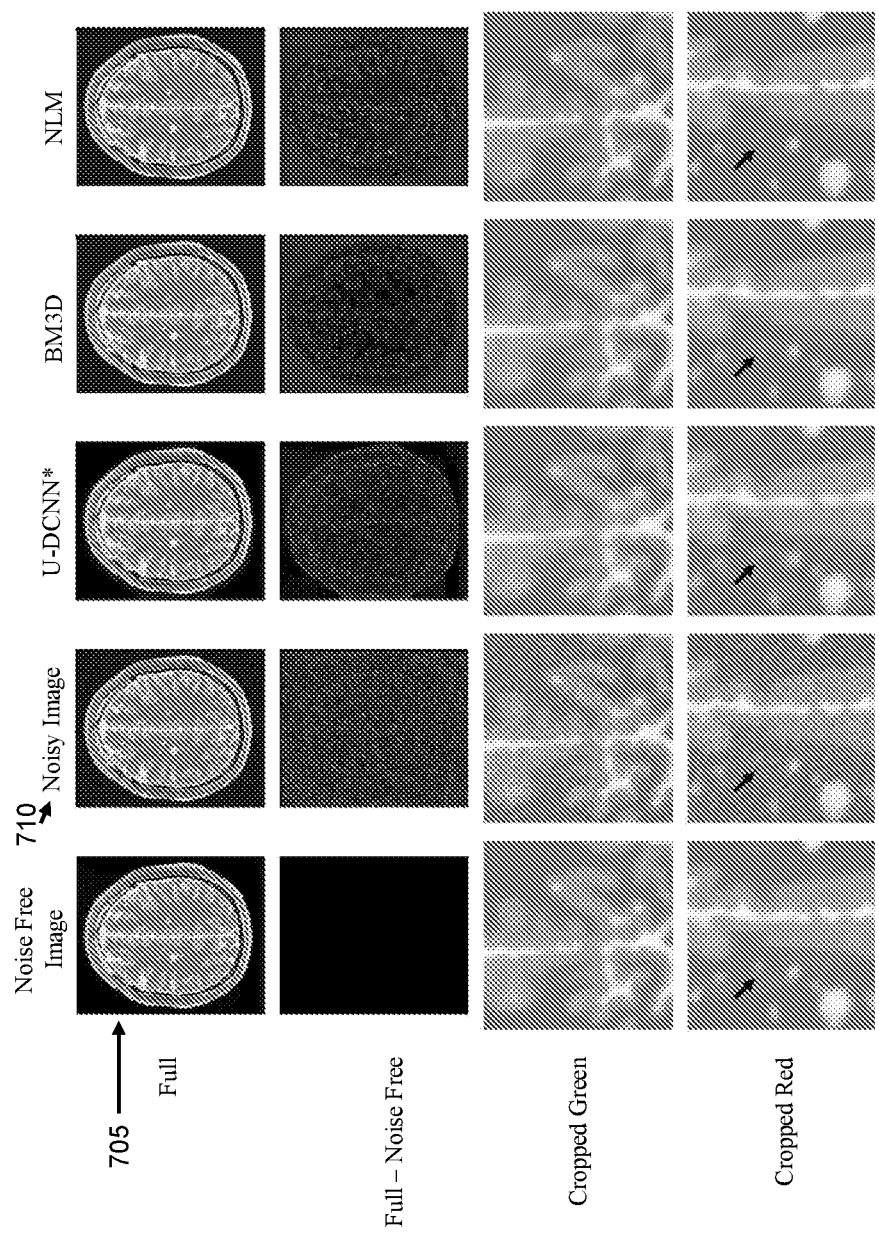
FIG. 7 illustrates a result from an experiment related to denoising a simulated MRI. An embodiment of the U-DCNN* is successful at suppressing a significant amount of noise and maintaining resolution. The arrows point to a region where the reference methods, BM3D and NLM, are unsuccessful in denoising the lesion region.

With reference to FIGS. 6 and 7, the noisy input images 625 can include noise data 710 and noise-free image data 705. According to some embodiments of the present disclosure, the noisy input images 625 are processed by running iterations of a converging sequence in the U-DCNN 600, and updating the parameter settings used in calculating a series of image feature sets with the U-DCNN 600. The parameter settings can be updated in each iteration 605 of the converging sequence. The converging sequence of the U-DCNN 600 can be terminated before the feature sets predict an output image 650 that replicates the noise data 710 from the noisy input image 625. According to some embodiments of the present disclosure, a denoised MR image 705 of the area of interest A can be output based on the selected features set.

Embodiments of the present disclosure may use different input images, network depths, and final connection layers. In some embodiments, the converging sequence may be terminated at a selected final set of parameter settings calculated during the iterations of the U-DCNN 600. According to some embodiments of the present disclosure, the iterations are constrained by structuring the U-DCNN 600 to include two layers of encoding 660, 670, and two layers of decoding 680, 690. In some embodiments the input image 625 is chosen as random values sampled from a normal distribution similar to a generative adversarial network, as in [4], and in some embodiments the first values of the U-DCNN's 600 weights and biases may be assigned randomly. In some embodiments, a Gaussian filter is applied to a noisy target image as the input. The Gaussian filter may be a Gaussian filter with a large standard deviation. The noisy input images 625 may also be down sampled by a selected factor prior to running iterations of the U-DCNN 600. For brain MRI, the filtered image can provide information about overall brain structure and a good estimation of regional intensity values. Therefore, the generation process may focus more on reconstructing the fine details missed from the filtered image and allows a faster convergence. In some embodiments, the U-DCNN 600 may include a U-Net that is a shallow or very shallow U-Net, such as a U-Net with only two layers. Embodiments including only two layers may have increased computational efficiency, and better maintain low level details. According to some embodiments of the present disclosure, the U-DCNN 600 can include encoding layers 630A, 630B, 630C, decoding layers 635A, 635B, 635C, and skip layers 640A, 640B, 640C with respective intermediate outputs 632A, 632B, 632C, 637A, 637B, 637C, and a higher percentage of the noise free image data 705 is processed through the intermediate layers, while a lower percentage of noise data 710 is processed through the intermediate layers prior to the converging sequence. Skip layer intermediate outputs (not separately shown) can be calculated using respective encoding layer intermediate outputs 632A, 632B, 632C from each encoding layer 630A, 630B, 630C, and the skip layer intermediate outputs (not separately shown) can be concatenated with respective decoding layer intermediate outputs 637A, 637B, 637C.

Some embodiments of the present disclosure include a final connection layer 655. The final connection layer 655 can perform convolutions on the input image and concatenate the results to the final set of features for output prediction. According to some embodiments of the present disclosure, the network can leverage information from the filtered input to correct errors caused by the reconstruction process. The final connection layer 655 may also help to make the range and distribution of predicted intensity values similar to the input. Additional embodiments incorporate more than one input to the U-DCNN 600, such as additional inputs configured from high signal to noise ratio image data gathered from selected acquisition sequences. In additional non-limiting embodiments of the disclosure, a method of denoising MR images includes acquiring high signal to noise ratio (SNR) MR image data in selected acquisition sequences and using using the high SNR MR image data in a series of additional input images to the U-DCNN. For each additional input image, the U-DCNN performs the steps of running iterations, updating parameter settings, and terminating the U-DCNN before respective noise data in the additional input images is fully replicated (i.e., the same U-DCNN structure is used to perform one of a plurality of denoising algorithms on both the noisy input images and additional input images; the calculations are performed in parallel). In these embodiments, forming a final denoised MR image uses the noisy input image and the additional input image to create an acceptable level of denoising in an output image. Processing steps for combining the results of the U-DCNN, as retrieved for noisy input images and additional high SNR input images, may vary according to the use at hand.

Embodiments of the present disclosure may be implemented as a system with one or more processors and a memory device coupled to the one or more processors, with the memory device storing instructions which can be executed by the one or more processors to cause the system to perform denoising using the U-DCNN 600. The system can include a display for viewing the denoised MR image 705 data for each iteration 605, and a user interface 158 that allows a user to select the number of iterations the system will perform. The system can also include a control system (not shown) that tracks the number of iterations completed for each view. A non-transitory computer readable medium can be configured to store instructions which cause a computer to perform the steps of some embodiments of the present disclosure.

Using this principle, design choices can to be made in implementation including selection of input, objective function, network structure and stopping criteria to determine the best strategy. An embodiment of the present disclosure uses a completely random input with uniform distribution was used, however, this can lead to instability and prolong the reconstruction time as no information about a specific image is available; however, using the noisy image itself behaves very similarly to denoising autoencoders and over-simplifies the reconstruction process and thus cannot achieve a good separation of the image and noise. Other options, such as a transformed noisy image with different low-pass filters or pre-processed image using NLM, may be used according to some embodiments of the present disclosure. With the noisy image as the reconstruction output, the absolute differences (l1), mean squared differences (l2) and a hybrid of the two can be used as potential objective functions. l2 may lead to over-smoothed results but has better gradient performance. In network structure, the number of layers, filters and other hyper-parameters are often very difficult to optimize due to the poorly understood theoretical effects of each parameter. The performance of the network may be related to the complexity of the network.

Various experiments were performed using embodiments of the present disclosure. In one experiment, in the encoding path, stride of 2 was used in the convolution modules to replace max-pooling. ADAM optimizer was used with a learning rate of 0.001. LeakyReLU was used as the activation function. Bilinear interpolation was used for upsampling. The loss function was the least squared errors (l2) between the network output and the noisy image. The number of features used in encoding convolutions ($n_E$) and in decoding convolutions ($n_D$) was 256. Number of features used in skipping ($n_S$) was 1. In this embodiment, outputs were selected after 440 iterations as the denoised result.

An embodiment of the present disclosure was compared to filter-based denoising algorithms. Two state-of-the-art filter-based approaches, NLM and BM3D were compared using their open-source implementations. NLM [1] takes the mean of all similar pixels in the image. BM3D [2] improves upon NLM by grouping similar 2D image fragments into 3D data arrays and uses 3D transformation to attenuate the noise. The parameter h for NLM was picked to be 1.7 and sigma was automatically optimized for each case, and set a sigma of 10 for BM3D, following the suggested best practice. The embodiment of the present disclosure was first analyzed on a simulated brain MR image to obtain the optimal network structure, and then validated on additional simulated brain MRI and an acquired MRI dataset.

Embodiments of the present disclosure may be applied to 2D images, 3D images, or both. Embodiments of the present disclosure applied to 3D images can use the additional spatial information from the through-plane dimension that is not present in a 2D image. The acquired MR image data 160 may include multi-slice or 3D acquisition. For example, a slice-wise sliding window technique using 3D convolutions can be used. For brain MRI with multi-slice 2D or 3D acquisitions, the spatial information along the through-plane dimension can be integrated to improve the performance [39A]. Replacing the 2D convolutions with 3D convolutions in the unsupervised DCNN can change it to a 3D network. According to some embodiments of the present disclosure, the network can take the entire 3D stack as an input. However, according to some embodiments of the present disclosure, a slice-wise sliding window can be used by reconstructing a small number of slices (e.g. 8) together and sliding to the next stack when one stack finishes denoising.

Using a slice-wise sliding window method can avoid the greatly increased computation and memory requirements of a network that takes the entire 3D stack as a single input. The network structure on the slice dimension will also be greatly simplified to limit the extra computations. To further accelerate the algorithm, which will become more of a bottleneck when there are a large number of slices in one scan, ShuffleNet [33] can be used. ShuffleNet divides the convolutions along the feature dimension into smaller groups and performs a two-step process to first run convolutions within groups and then summarizes the output from different groups. ShuffleNet has shown advantages in computation speed with minimal or no loss of accuracy.

As the unsupervised DCNN is used for denoising, the requirement for collecting a large dataset for training and validation is alleviated. However, a decent-sized validation dataset that uses a variety of sequences and acquisition strategies is still necessary. To evaluate the algorithm against a noise-free gold standard and compare with other methods, an open source simulated brain database (BrainWeb) [34A-38A] that includes T1, T2 and PD weighted images at a variety of slice thicknesses, noise levels, and levels of intensity non-uniformity was used. It also includes both a normal brain and a brain with MS lesions.

The simulated MR images were obtained from Brainweb [5], which provides noise-free images as the ground-truth for quantitative analysis. Two T2-weighted images with two different noise levels at 3% and 5% were simulated. The noise in the simulated images has a Rician distribution. The noise level represents the percent ratio of the standard deviation of the white Gaussian noise versus the signal for cerebrospinal fluid. The selected slices have a common dimension of 217×181 with an isotropic voxel size of 1 mm×1 mm.

The acquired MRI was obtained using a T2-weighted sequence with Half-Fourier Acquisition Single-shot Turbo spin Echo imaging (HASTE) [6] on a Siemens 3T Trio scanner equipped with 32-channel head coil. The Generalized Autocalibrating Partially Parallel Acquisitions (GRAPPA) [7] with acceleration factor 3 was used for even faster acquisition. Due to the B1 inhomogeneity and enhanced g-factor noise from GRAPPA, the resulting noise is non-uniform and relatively high at the center of the brain. The selected 2D slice has a dimension of 320×300 with an isotropic voxel size of 0.69 mm×0.69 mm.

As the noise level for most of the actual MRI is below 5%, an embodiment of the present disclosure was tested with different variations at 3% noise level. Table 1 depicts a quantitative evaluation in terms of mean(std) obtained by different denoising methods on a simulated MRI slice. The displayed methods include the five proposed variants of U-DCNN 600 and two filter-based denoising approaches. L stands for number of layers. Each network variant in Table 1 was tested 10 times for an accurate evaluation.

TABLE 1

| Method | Input Image | L | Final Connection | RMSE | PSNR | SSIM |
| --- | --- | --- | --- | --- | --- | --- |
| U-DCNN1 | Random | 5 | No | 0.030(0.006) | 30.245(1.654) | 0.813(0.047) |
| U-DCNN2 | Random | 2 | No | 0.031(0.002) | 29.915(0.435) | 0.745(0.012) |
| U-DCNN3 | Filtered | 5 | No | 0.029(0.002) | 30.591(0.488) | 0.808(0.030) |
| U-DCNN4 | Filtered | 2 | No | 0.024(0.002) | 32.198(0.777) | 0.914(0.026) |
| U-DCNN* | Filtered | 2 | Yes | 0.023(0.002) | 32.317(0.796) | 0.920(0.009) |
| NLM | | | | 0.027 | 31.297 | 0.800 |
| BM3D | | | | 0.027 | 32.875 | 0.799 |

Table 2 depicts a quantitative evaluation with different denoising methods on 2 simulated MRI datasets. The listed scores are the average of 181 slices in each MRI.

TABLE 2

| Noise Level | Methods | RMSE | PSNR | SSIM |
| --- | --- | --- | --- | --- |
| 3% | U-DCNN* | 0.037 | 28.469 | 0.825 |
| | NLM | 0.037 | 28.407 | 0.766 |
| | BM3D | 0.027 | 31.556 | 0.767 |
| 5% | U-DCNN* | 0.060 | 23.881 | 0.728 |
| | NLM | 0.062 | 23.710 | 0.691 |
| | BM3D | 0.045 | 26.946 | 0.708 |

Results obtained from an embodiment of the present disclosure including a U-DCNN* with Gaussian filtered input, 2 layers, and a final connection were compared to results of two other filtering methods, NLM and BM3D. As shown in Table 1, the embodiment of the present disclosure including a U-DCNN* performed similarly in terms of PSNR to NLM and BM3D, and outperformed them in terms of RMSE and SSIM. Qualitatively, as shown in FIG. 7, the embodiment of the present disclosure including a U-DCNN* successfully denoised the lesions and gray matter. In one non-limiting result of experimentation, BM3D and NLM erased small pathological regions as pointed in FIG. 7, while U-DCNN* did not.

First, an embodiment of the present disclosure including a U-DCNN* was applied to the same dataset as NLM and BM3D. The dataset included 181 slices of a simulated MRI dataset at 5% and 3% noise, respectively. Then, for each method and each evaluation metric, the average of 181 slices was calculated, as shown in Table 2. The embodiment of the present disclosure including a U-DCNN* had the highest SSIM, which suggests its superiority in reconstructing image structures.

Figure 8:
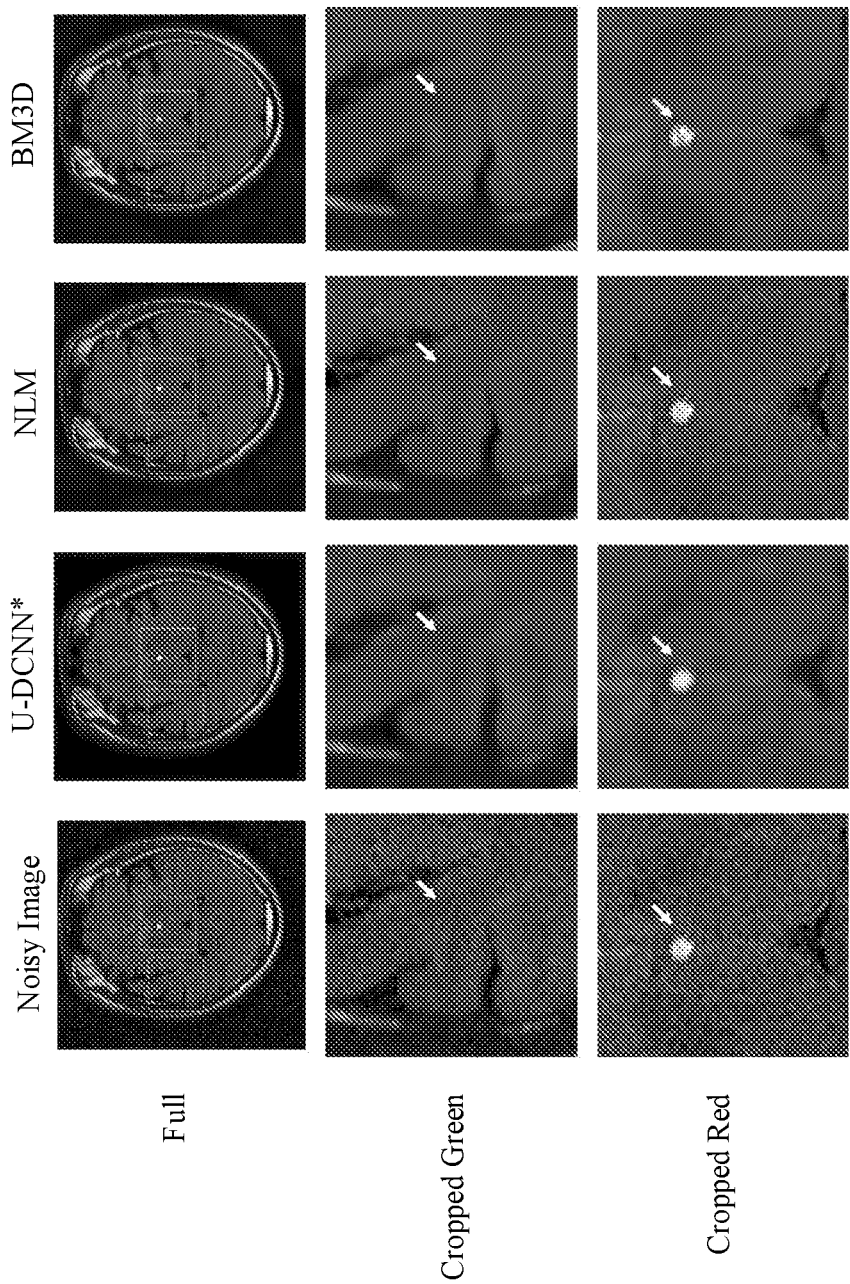
FIG. 8 illustrates a result from an experiment related to denoising an acquired MR image. An embodiment of the U-DCNN* is successful at denoising regions with different noise levels while maintaining the contrast and fine structures. Reference models are BM3D and NLM. The arrows in the second row demonstrate the superiority of some embodiments in maintaining the gray-white matter contrast. The arrows in the third row show that NLM and BM3D are unable to keep the fine structure when denoising while some embodiments of the U-DCNN* do not have this issue.

An embodiment of the present disclosure including a U-DCNN* was tested using the acquired MRI dataset. Since NLM with previous optimized smoothness factor h=1.7 cannot suppress any noise due to the non-uniform noise distribution, h was increased to 2.5. In addition, as there is no ground-truth, no quantitative comparisons can be made. FIG. 8 shows the visual comparison between U-DCNN* and the two reference methods. With an increased smoothing factor, NLM still did not denoise as much as U-DCNN* in the center, where the noise level is much enhanced. Additionally, both reference methods significantly reduced contrast between the gray matter and white matter, as shown in the second row of FIG. 8. For BM3D, although it yielded a much smoother image, it lost or altered many fine structures, as shown in the pointed region in the third row of FIG. 8. Thus, for this acquired MR image, an embodiment of the present disclosure including U-DCNN* shows a clear advantage over NLM and BM3D.

Conclusion

The specific configurations, choice of materials and the size and shape of various elements can be varied according to particular design specifications or constraints requiring a system or method constructed according to the principles of the present disclosure. Such changes are intended to be embraced within the scope of the present disclosure. The presently disclosed embodiments, therefore, are considered in all respects to be illustrative and not restrictive. The patentable scope of certain embodiments of the present disclosure is indicated by the appended claims, rather than the foregoing description.

LIST OF REFERENCES

[1] Buades, A., Coll, B., Morel, J.-M.: Non-Local Means Denoising. Image Processing On Line. 1, (2011).
[2] Dabov, K., Foi, A., Katkovnik, V., Egiazarian, K.: Image denoising with block-matching and 3D filtering. Image Processing: Algorithms and Systems, Neural Networks, and Machine Learning. (2006).
[3] Zhang, K., Zuo, W., Chen, Y., Meng, D., Zhang, L.: Beyond a Gaussian Denoiser: Residual Learning of Deep CNN for Image Denoising. IEEE Transactions on Image Processing. 26, 3142-3155 (2017).
[4] Ulyanov, D., Vedaldi, A., Lempitsky, V.: Deep image prior. arXiv Preprints. (2017).
[5] Cocosco, C. A., Kollokian, V., Kwan, R. K., Evans, A. C.: BrainWeb: Online Interface to a 3D MRI Simulated Brain Database. NeuroImage. 5, (1997).
[6] Patel, M. R., Klufas, R. A., Alberico, R. A., Edelman, R. R.: Half-fourier acquisition single-shot turbo spin-echo (HASTE) MR: comparison with fast spin-echo MR in diseases of the brain. American Journal of Neuroradiology. 18, 1635-1640 (1997).
[7] Griswold, M. A., Jakob, P. M., Heidemann, R. M., Nittka, M., Jellus, V., Wang, J., Kiefer, B.: Generalized autocalibrating partially parallel acquisitions (GRAPPA). Magnetic Resonance in Medicine. 47, 1202-1210 (2002).
[8] Çiçek, Özgün et al., 3D U-Net: Learning Dense Volumetric Segmentation from Sparse Annotation published in MICCAI 2016.
[9] Silva, Thalles, An intuitive introduction to Generative Adversarial Networks (GANs; https://www.freecodecamp.org/news/an-intuitive-introduction-to-generative-adversarial-networks-gans-7a2264a81394/ (accessed on Apr. 22, 2020).

LIST OF SUPPLEMENTAL REFERENCES

[1A] Haysteen I, Ohlhues A, Madsen K H, et al. Are Movement Artifacts in Magnetic Resonance Imaging a Real Problem?—A Narrative Review. Front Neurol. 2017; 8:232. doi: 10.3389/fneur.2017.00232. PMCID: PMC5447676.
[2A] Edwards A D, Arthurs O J. Paediatric MRI under sedation: is it necessary? What is the evidence for the alternatives? Pediatr Radiol. 2011; 41(11):1353-1364. doi: 10.1007/s00247-011-2147-7.
[3A] McGibney G, Smith M R, Nichols S T, Crawley A. Quantitative evaluation of several partial Fourier reconstruction algorithms used in MRI. Magn Reson Med. 1993; 30(1):51-59.
[4A] Pruessmann K P, Weiger M, Scheidegger M B, Boesiger P. SENSE: sensitivity encoding for fast MRI. Magn Reson Med. 1999; 42(5):952-962.
[5A] Griswold M A, Jakob P M, Heidemann R M, et al. Generalized autocalibrating partially parallel acquisitions (GRAPPA). Magn Reson Med. 2002; 47(6):1202-1210.
[6A] Lustig M, Pauly J M. SPIRiT: Iterative self-consistent parallel imaging reconstruction from arbitrary k-space. Magn Reson Med. 2010; 64(2):451-471. doi: 10.1002/mrm.22428. PMCID: PMC2925465.
[7A] Lustig M, Donoho D, Pauly J M. Sparse MRI: The application of compressed sensing for rapid MR imaging. Magn Reson Med. 2007; 58(6):1182-1195.
[8A] Glover G H, Li T Q, Ress D. Image-based method for retrospective correction of physiological motion effects in fMRI: RETROICOR. Magn Reson Med. 2000; 44(1):162-167.
[9A] Maclaren J, Herbst M, Speck O, Zaitsev M. Prospective motion correction in brain imaging: a review. Magn Reson Med. 2013; 69(3):621-636. doi: 10.1002/mrm.24314.
[10A] Buades A, Coll B, Morel J. A non-local algorithm for image denoising. In Proc. 2005 IEEE Computer Society Conference on Computer Vision and Pattern Recognition (CVPR'05), San Diego, CA, USA, 2005, pp. 60-65, vol. 2. doi: 10.1109/CVPR.2005.38.
[11A] Coupe P, Yger P, Prima S, Hellier P, Kervrann C, Barillot C. An optimized blockwise nonlocal means denoising filter for 3-D magnetic resonance imaging. IEEE Trans Med Imaging. 2008; 27(4):425-441. doi: 10.1109/TMI.2007.906087.
[12A] Chang L, ChaoBang G, Xi Y. A MRI denoising method based on 3D nonlocal means and multidimensional PCA. Comput Math Methods Med. 2015; 232389. doi: 10.1155/2015/232389.
[13A] Bhujle H V, Chaudhuri S. Laplacian based non-local means denoising of MR images with rician noise. Magn Reson Imaging. 2013; 31(9):1599-1610. doi: 10.1016/j.mri.2013.07.001.
[14A] Zhang X, Hou G, Ma J, et al. Denoising MR images using non-local means filter with combined patch and pixel similarity. PLoS One. 2014; 9(6):e100240. doi: 10.1371/journal.pone.0100240.

[15A] Manjon J V, Coupe P, Marti-Bonmati L, Collins D L, Robles M. Adaptive non-local means denoising of MR images with spatially varying noise levels. J Magn Reson Imaging. 2010; 31(1):192-203. doi: 10.1002/jmri.22003.

[16A] Dabov K, Foi A, Katkovnik V, Egiazarian K. Image denoising with block-matching and 3D filtering. In Proc. SPIE 6064, Image Processing: Algorithms and Systems, Neural Networks, and Machine Learning, 606414. doi: 10.1117/12.643267.

[17A] Zhao T, Hoffman J, McNitt-Gray M, Ruan D. Ultra-low-dose CT image denoising using modified BM3D scheme tailored to data statistics. Med Phys. 2019; 46(1): 190-198. doi: 10.1002/mp.13252.

[18A] Lyu Q, Yang C, Gao H, et al. Technical Note: Iterative megavoltage CT (MVCT) reconstruction using block-matching 3D-transform (BM3D) regularization. Med Phys. 2018; 45(6):2603-2610. doi: 10.1002/mp.12916.

[19A] Harrison A P, Xu Z, Pourmorteza A, Bluemke D A, Mollura D J. A multichannel block-matching denoising algorithm for spectral photon-counting CT images. Med Phys. 2017; 44(6):2447-2452. doi: 10.1002/mp.12225.

[20A] Jiang D, Dou W, Vosters L, Xu X, Sun Y, Tan T. Denoising of 3D magnetic resonance images with multi-channel residual learning of convolutional neural network. Jpn J Radiol. 2018; 36(9):566-574. doi: 10.1007/s11604-018-0758-8.

[21A] Zhang K, Zuo W, Chen Y, Meng D, Zhang L. Beyond a Gaussian Denoiser: Residual Learning of Deep CNN for Image Denoising. IEEE Trans Image Process. 2017; 26(7):3142-3155. doi: 10.1109/TIP.2017.2662206.

[22A] Benou A, Veksler R, Friedman A, Riklin Raviv T. Ensemble of expert deep neural networks for spatio-temporal denoising of contrast-enhanced MRI sequences. Med Image Anal. 2017; 42:145-159. doi:10.1016/j.media.2017.07.006.

[23A] Vincent P, Larochelle H, Lajoie I, Bengio Y, Manzagol P A. Stacked Denoising Autoencoders: Learning Useful Representations in a Deep Network with a Local Denoising Criterion. J Mach Learn Res. 2010; 11:3371-3408.

[24A] Ulyanov D, Vedaldi A, Lempitsky V. Deep image prior. arXiv Preprints. 2017. arXiv:1711.10925.

[25A] Goodfellow I J, Pouget-Abadie J, Mirza M, et al. Generative Adversarial Networks. arXiv Preprints. 2014. arXiv:1406.2661.

[26A] Macovski A. Noise in MRI. Magn Reson Med. 1996; 36(3):494-497.

[27A] Gudbjartsson H, Patz S. The Racian distribution of noisy MRI data. Magn Reson Med. 1995; 34(6):910-914.

[28A] Thunberg P, Zetterberg P. Noise distribution in SENSE- and GRAPPA-reconstructed images: a computer simulation study. Magn Reson Imaging. 2007; 25(7): 1089-1094.

[29A] Aja-Fernandez S, Vegas-Sanchez-Ferrero G, Tristan-Vega A. Noise estimation in parallel MRI: GRAPPA and SENSE. Magn Reson Imaging. 2014; 32(3):281-290. doi: 10.1016/j.mri.2013.12.001.

[30A] Patrella J R, Provenzale J M. MR Perfusion imaging of the brain: techniques and applications. AJR Am J Roentgenol. 2000; 175(1):207-219.

[31A] Wang Z, Bovid A C, Sheikh H R, Simoncelli E P. Image quality assessment: from error visibility to structural similarity. IEEE Trans Image Process. 2004; 13(4): 600-612. doi: 10.1109/TIP.2003.819861.

[32A] Shin H C, Roth H R, Gao M, et al. Deep Convolutional Neural Networks for Computer-Aided Detection: CNN Architectures, Dataset Characteristics and Transfer Learning. IEEE Trans Med Imaging. 2016; 35(5):1285-1298. doi: 10.1109/TMI.2016.2528162. PMCID: PMC4890616.

[33A] Zhang X, Zhou X, Lin M, Sun J. ShuffleNet: An Extremely Efficient Convolutional Neural Network for Mobile Devices. arXiv Preprints. 2017. arXiv: 1707.01083.

[34A] http://www.bic.mni.mcgill.ca/brainweb/

[35A] Cocosco C A, Kollokian V, Kwan R K, Evans A C. BrainWeb: Online Interface to a 3D MRI Simulated Brain Database. NeuroImage, 1997; 5(4):5425.

[36A] Kwan R K, Evans A C, Pike G B. MRI simulation-based evaluation of image-processing and classification methods. IEEE Trans Med Imaging. 1999; 18(11):1085-1097.

[37A] Kwan R K, Evans A C, Pike G B. An Extensible MRI Simulator for Post-Processing Evaluation. Visualization in Biomedical Computing (VBC'96). Lecture Notes in Computer Science, vol. 1131. Springer-Verlag, 1996. 135-140.

[38A] Collins D L, Zijdenbos A P, Kollokian V, et al. Design and Construction of a Realistic Digital Brain Phantom. IEEE Trans Med Imaging. 1998; 17(3):463-468.

[39A] Maggioni M, Katkovnik V, Egiazarian K, Foi A. Nonlocal transform-domain filter for volumetric data denoising and reconstruction. IEEE Trans Image Process. 2013; 22(1):119-133. doi: 10.1109/TIP.2012.2210725.

[40A] Saloner D. The AAPM/RSNA physics tutorial for residents. An introduction to MR angiography. Radiographics. 1995; 15(2):453-465.

[41A] Hartung M P, Grist T M, Francois C J. Magnetic resonance angiography: current status and future directions. J Cardiovasc Magn Reson. 2011; 13:19. doi: 10.1186/1532-429X-13-19. PMCID: PMC3060856.

[42A] Ghavhan G B, Babyn P S, Thomas B, Shroff M M, Haacke E M. Principles, techniques, and applications of T2*-based MR imaging and its special applications. Radiographics. 2009; 29(5):1433-1449. doi: 10.1148/rg.295095034. PMCID: PMC2799958.

[43A] Schaefer P W, Grant P W, Gonzalez R G. Diffusion-weighted MR imaging of the brain. Radiology. 2000; 217(2):331-345.

[44A] Patrella J R, Provenzale J M. MR Perfusion Imaging of the Brain Techniques and Applications. AJR Am J Roentgenol. 2000; 175(1):207-219.

[45A] Zhao L, Fielden S W, Feng X, Wintermark M, Muger JP 3rd, Meyer C H. Rapid 3D dynamic arterial spin labeling with a sparse model-based image reconstruction. Neuroimage. 2015; 205-216. doi: 10.1016/j.neuroimage.2015.07.018. PMCID: PMC4615585.

[46A] Feng X, Salerno M, Kramer C M, Meyer C H. Kalman filter techniques for accelerated Cartesian dynamic cardiac imaging. Magn Reson Med. 2013; 69(5): 1346-1356. doi: 10.1002/mrm.24375. PMCID: PMC3536913.

[47A] Feng X, Tustison N, Meyer C H. Brain Tumor Segmentation using an Ensemble of 3D U-Nets and Overall Survival Prediction using Radiomic Features. arXiv Preprints. 2018. arXiv:1812.01049.

What is claimed is:

1. A computer-implemented method of denoising a magnetic resonance (MR) image, comprising:
acquiring magnetic resonance (MR) image data of an area of interest of a subject, wherein the image data comprises noisy input images, and wherein the noisy input images comprise noise data and noise free image data;
for each of the noisy input images:

running iterations of a converging sequence in an unsupervised deep convolutional neural network (U-DCNN);

in each iteration, updating parameter settings used in calculating a series of image feature sets with the U-DCNN, the image feature sets predicting an output image;

terminating the converging sequence of the U-DCNN before the feature sets predict a respective output image that replicates all of the noise data from the noisy input image; and outputting, based on a selected feature set, a denoised MR image of the area of interest of the subject.

2. The method of claim 1, comprising terminating the converging sequence at a selected final set of the parameter settings calculated during the iterations of the U-DCNN.

3. The method of claim 2, comprising randomly assigning first values to weights and biases in the parameter settings.

4. The method of claim 1, wherein the U-DCNN comprises encoding layers, decoding layers and skip layers with respective intermediate outputs, and wherein the method further comprises processing a higher percentage of noise free image data through the intermediate layers relative to a lower percentage of noise data through the intermediate layers prior to the step of terminating the converging sequence.

5. The method of claim 4, further comprising constraining the iterations by structuring the U-DCNN with two layers of encoding and an additional two layers of decoding.

6. The method of claim 5, further comprising:
calculating a series of skip layer intermediate outputs using respective encoding layer intermediate outputs from each encoding layer; and
concatenating respective skip layer intermediate outputs with a respective decoding layer intermediate output.

7. The method of claim 1, further comprising applying a Gaussian filter to respective noisy input images prior to running iterations of the U-DCNN.

8. The method of claim 1, further comprising down sampling the respective noisy images by a selected factor prior to running iterations of the U-DCNN.

9. The method of claim 1, wherein the acquiring the MR image data comprises multi-slice or 3D acquisition, and wherein the denoising incorporates spatial information from a through-plane dimension of the MR image data.

10. The method of claim 9, wherein the U-DCNN is configured for 3D convolution, and wherein the denoising comprises reconstructing a first stack of the acquired slices together, and reconstructing a second stack of the acquired slices together after denoising the first stack of the acquired slices.

11. The method of claim 1, wherein the area of interest of the subject is at least a part of the brain of the subject.

12. The method of claim 1, further comprising:
acquiring high signal to noise ratio (SNR) MR image data in selected acquisition sequences;
using the high SNR MR image data in a series of additional input images to the U-DCNN;
for each additional input image, performing the steps of running iterations, updating parameter settings, and terminating the U-DCNN before respective noise data in the additional input images is fully replicated; and
forming a final denoised MR image using the noisy input image and the additional input image.

13. The method of claim 1, wherein the denoising of the MR image is performed as part of magnetic resonance angiography, diffusion MRI, or perfusion MRI.

14. The method of claim 1, wherein the high SNR image data comprises MR image data acquired in T1, T2, or proton density (PD) sequences.

15. A system for denoising a magnetic resonance (MR) image, comprising:
one or more processors;
a memory device coupled to the one or more processors and storing instructions which, when executed by the one or more processors, cause the system to perform functions that include:
acquiring magnetic resonance (MR) image data of an area of interest of a subject, wherein the image data comprises noisy input images, and wherein the noisy input images comprise noise data and noise free image data;
for each of the noisy input images:
running iterations of a converging sequence in an unsupervised deep convolutional neural network (U-DCNN);
in each iteration, updating parameter settings used in calculating a series of image feature sets with the U-DCNN, the image feature sets predicting an output image;
terminating the converging sequence of the U-DCNN before the feature sets predict a respective output image that replicates all of the noise data from the noisy input image; and
outputting, for each iteration, an updated compilation of denoised MR image data of the area of interest of the subject.

16. The system of claim 15, further comprising a display configured to provide a view of the updated compilation of denoised MR image data for each iteration.

17. The system of claim 15 or 16, further comprising a user interface configured to receive a selected number of iterations at which the system terminates the converging sequence.

18. The system of claim 17, further comprising a control system configured to track a number of iterations completed for each view.

19. The system of claim 15, wherein the noise data comprises non-uniform noise originating from coils used in multi-band MR image acquisitions.

20. The system of claim 15, wherein a plurality of the noisy input images are previously calculated as diagnostic compilations of acquired image data from parallel channels.

21. The system of claim 20, wherein the diagnostic compilations comprise calculated images showing at least one of the subject's apparent diffusion coefficient (ADC), cerebral blood flow (CBF) and cerebral blood volume (CBV).

22. A non-transitory computer-readable medium storing instructions thereon which, when executed by one or more processors, cause a computer to perform functions for denoising a magnetic resonance (MR) image that include:
acquiring magnetic resonance (MR) image data of an area of interest of a subject, wherein the image data comprises noisy input images, and wherein the noisy input images comprise noise data and noise free image data;
for each of the noisy input images:
running iterations of a converging sequence in an unsupervised deep convolutional neural network (U-DCNN);
in each iteration, updating parameter settings used in calculating a series of image feature sets with the U-DCNN, the image feature sets predicting an output image;

terminating the converging sequence of the U-DCNN before the feature sets predict a respective output image that replicates all of the noise data from the noisy input image; and outputting, based on a selected feature set, a denoised MR image of the area of interest of the subject.

* * * * *